United States Patent
Dakin et al.

(10) Patent No.: US 7,410,489 B2
(45) Date of Patent: Aug. 12, 2008

(54) INTERNAL CORD FIXATION DEVICE

(75) Inventors: Edward B. Dakin, Lindsay (CA);
Albert L. Lippincott, III, Prior Lake, MN (US)

(73) Assignee: Daos Limited, Markham, Ontario (CA)

( * ) Notice: Subject to any disclaimer, the term of this patent is extended or adjusted under 35 U.S.C. 154(b) by 738 days.

(21) Appl. No.: 10/629,007

(22) Filed: Jul. 29, 2003

(65) Prior Publication Data

US 2004/0127907 A1    Jul. 1, 2004

Related U.S. Application Data

(63) Continuation-in-part of application No. 10/115,446, filed on Apr. 2, 2002, now abandoned, which is a continuation of application No. 09/162,036, filed on Sep. 28, 1998, now Pat. No. 6,368,326.

(51) Int. Cl.
  *A61B 17/58* (2006.01)
  *A61B 17/04* (2006.01)
(52) U.S. Cl. ............................ 606/103; 606/72; 606/232
(58) Field of Classification Search .................... 606/72, 606/74, 103, 232, 228–231, 76, 77; 24/298, 24/300, 135 R; 623/13.15, 13.16, 13.19, 623/13.12
  See application file for complete search history.

(56) References Cited

U.S. PATENT DOCUMENTS

| 887,074   | A |  5/1908  | Dapage     |
|-----------|---|----------|------------|
| 2,143,922 | A |  1/1939  | Longfellow |
| 2,501,978 | A |  3/1950  | Wichman    |
| 3,477,429 | A | 11/1969  | Sampson    |
| 3,709,218 | A |  1/1973  | Halloran   |
| 3,896,500 | A * | 7/1975 | Rambert et al. .......... 623/13.14 |

(Continued)

FOREIGN PATENT DOCUMENTS

DE    1958429    7/1971

(Continued)

OTHER PUBLICATIONS

Howmedica, The Dall-Miles Cable Grip System (1995).

(Continued)

*Primary Examiner*—Julian W. Woo
(74) *Attorney, Agent, or Firm*—Fredrikson & Byron, P.A.

(57) ABSTRACT

Methods and apparatuses for fixing a bone fragment or a bone prosthesis onto a bone. To affix a bone fragment to the bone, an internal fastener is attached from within the interior of the bone to a bone fragment with a length of flexible, inelastic cord extending within the bone interior and attached to the fastener and passing outwardly through an opening in a second bone fragment. An axially rigid tubular support may be placed along the cord to reduce particulate shedding, to reduce ingrowth of bone into the cord, to provide compressive resistance to the cable, or to deliver antibiotics or other pharmaceuticals. The fastener and cord are so positioned as to draw respective fracture surfaces together to reduce the fracture when the cord is pulled outwardly of the opening in the second bone fragment. A second fastener desirably is attached to the bone opening, this fastener including an open bore to receive the cord and a lock to secure the cord to this fastener and maintain the cord under tension.

51 Claims, 26 Drawing Sheets

U.S. PATENT DOCUMENTS

| | | | |
|---|---|---|---|
| 3,953,896 A * | 5/1976 | Treace | 623/13.12 |
| 3,997,138 A | 12/1976 | Crock et al. | |
| 4,041,939 A | 8/1977 | Hall | |
| 4,047,523 A | 9/1977 | Hall | |
| 4,050,464 A | 9/1977 | Hall | |
| 4,120,298 A | 10/1978 | Fixel | |
| 4,146,022 A | 3/1979 | Johnson et al. | |
| 4,492,226 A | 1/1985 | Belykh et al. | |
| 4,587,963 A | 5/1986 | Leibinger et al. | |
| 4,708,132 A | 11/1987 | Silverstrini | |
| 4,790,303 A | 12/1988 | Steffee | |
| 4,790,850 A * | 12/1988 | Dunn et al. | 623/13.19 |
| 4,889,110 A | 12/1989 | Galline et al. | |
| 4,976,712 A | 12/1990 | Vanderslik | |
| 4,976,740 A | 12/1990 | Kleiner | |
| 5,013,314 A | 5/1991 | Firica et al. | |
| 5,108,397 A | 4/1992 | White | |
| 5,116,340 A | 5/1992 | Songer et al. | |
| 5,156,616 A | 10/1992 | Meadows et al. | |
| 5,201,733 A | 4/1993 | Etheredge, III | |
| 5,306,290 A | 4/1994 | Martins et al. | |
| 5,312,410 A | 5/1994 | Miller et al. | |
| 5,324,291 A | 6/1994 | Ries et al. | |
| 5,395,374 A | 3/1995 | Miller et al. | |
| 5,449,361 A | 9/1995 | Preissman | |
| 5,454,812 A | 10/1995 | Lin | |
| 5,474,554 A | 12/1995 | Ku | |
| 5,536,270 A | 7/1996 | Songer et al. | |
| 5,562,668 A | 10/1996 | Johnson | |
| 5,569,253 A | 10/1996 | Farris et al. | |
| 5,571,139 A | 11/1996 | Jenkins, Jr. | |
| 5,611,801 A | 3/1997 | Songer | |
| 5,720,765 A | 2/1998 | Thal | |
| 5,788,697 A | 8/1998 | Kilpela et al. | |
| 5,797,913 A | 8/1998 | Dambreville et al. | |
| 5,921,986 A | 7/1999 | Bonutti | |
| 6,068,648 A | 5/2000 | Cole et al. | |
| 2003/0187444 A1 * | 10/2003 | Overaker et al. | 606/72 |

FOREIGN PATENT DOCUMENTS

| | | |
|---|---|---|
| EP | 0298400 | 1/1989 |
| EP | 576337 | 6/1993 |
| WO | WO9811838 | 3/1998 |

OTHER PUBLICATIONS

Zimmer, Cable-Ready Cable Grip System (Aug. 1994).

Mears D.C., Shirahama M., Stabilization of an Acetabular Fracture with Cables for Acute Total Hip Arthroplasty, The Journal of Arthroplasty, vol. 13, No. 1, pp. 104-107 (1998).

Labitzke R. Von der "Knochennacht" zu zeitgenossischen Osteosyntheseneine Chronologie Chirurg 66: pp. 452-458 (1995).

Dall D.M., Miles A.W., Re-attachment of the Greater Trochanter The Use of the Trochanter Cable-Grip System, JBJS (British), vol. 65-B, No. 1, pp. 55-59 (Jan. 1983).

Labitzke R., Schramm G., Witzel U., Quisthout P., "Sleeve-Rope Closure" of the Median Sternotomy after Open Heart Operations, Thorac. Cardiovasc. Surgeon 31, pp. 127-128 (1983).

Labitzke R., Drahtseile und intraossare Druckverteilungs-chulsenin der Chirurgie, Chirurg 53: pp. 741-743 (1982).

Labitzke R., Towfigh H., Operationstechnik und behandlung-sergebnisse nach lateraler Zuggurtung an Patella und Olecranon, Unfallheikunde 83, pp. 450-456 (1980).

Meeder P.J., Wentzensen A., Weise K., Die operative Behandlung der frischen acromino-clavicularen Luxation (Tossy III) durch Naht der Ligamente und Kirschner-Drahtzuggurtung, Langenbacks Arch. Chir. 350, pp. 169-173 (1980).

Schweiberer Von L., Operative Behandlung von Patellafrakturen, Zentralblatt fur Chirurgie, Heft 16, pp. 982-987 (1977).

Labitzke R., Die laterale Zuggurtung, Arch. Orthop. Unfall-Chir. 81, pp. 193-198 (1975).

Labitzke R., Statisch-experimentelle Untersuchungen zur Zuggurtun (dargestellt an der Olecranofraktur) Mschr. Unfallheilk. 78, pp. 393-400 (1975).

Labitzke R., Bipolar interfragmentare Druckkraftmessung am Modellknochen bei Variierung der Zuggurtung einer Olecranonfraktur, Arch. Orthop. Unfall-Chir. 81, pp. 199-205 (1975).

Labitzke R., Rehn J., Zur Behandlung von Patellafrakturen, Arch orthop. Unfal-Chir. 77, pp. 64-74 (1973).

Latizke R., Kehr H, Rehn J., Zur Behandlung von Olecranon-Frakturen und Olecranon-Pseudarthrosen, Arch. Orthop. Unfall-Chir. pp. 247-256 (1972).

Labitzeke R., Uberlegungen zur Theorie der Zuggurtung, Arch. Orthop. Unfall-Chir. 81, pp. 179-192 (1975).

* cited by examiner

INTERNAL CORD FIXATION DEVICE

This is a continuation-in-part of U.S. patent application Ser. No. 10/115,446, filed Apr. 2, 2002, now abandoned, which is a continuation of U.S. patent application Ser. No. 09/162,036, filed Sep. 28, 1998, now U.S. Pat. No. 6,368,326.

FIELD OF THE INVENTION

This invention pertains to the field of fixation devices for bones.

BACKGROUND OF THE INVENTION

Simple fractures of bones are readily treated by bringing the fracture surfaces together and holding them in the desired orientation with respect to one another through the use of splints, casts and the like. Bones in general have dense outer, strong cortical portions and interior, non-cortical portions that may include cancellous bone.

Comminuted fractures and fractures involving the breakage of a bone into numerous bone fragments are especially difficult to deal with since one must attempt to reposition each bone fragment in an orientation relative to each other bone fragment such that the fragments may knit together properly. For this purpose, physicians have often used metal plates that attach to the outer cortical surfaces of the bones and which utilize bone screws to hold the bone fragments in the desired position.

Another method for treating such fractures involves the use of cerclage procedures in which a wire is, in effect, wrapped about a broken bone to hold the fragments in place, the cerclage wire occasionally penetrating through the bone. Reference is made to Johnson et al., U.S. Pat. No. 4,146,002. Yet another method taught in Berger, U.S. Pat. No. 5,658,310, involves anchoring the balloon portion of a balloon catheter in the medullary cavity at one end of a long bone having a transverse fracture, and stretching the remaining portion of the elastic catheter across the fracture interface within the bone to maintain the fracture interface in compression. It would appear that unless the elastic catheter traverses the precise center of the bone at the fracture site (which may be difficult to accomplish, considering the bowed or curved nature of most bones), compressive forces will be uneven across the fracture site. That is, the compressive forces on the side of the bone nearest the catheter will be greater than the compressive forces on the opposite side of the bone, generating an unwanted bending moment across the fracture site.

With cerclage procedures, one must entirely encircle a bone in order to hold the bony parts together. Surgical procedures used to mount bone plates and cerclage elements to a bone often require supportive tissue that is normally joined to the bone to be cut from the bony tissue to enable direct visual access to the bone.

Procedures using bone plates and cerclage elements often tend to interrupt blood flow to the damaged bone fragments, thus hindering the healing process. Moreover, the use of bone plates and cerclage elements, particularly the former, can lead to stress shielding of the fracture site. While Wolff's Law teaches that bone growth is stimulated when stress is applied, continuous, excessive pressure applied to a bone may cause unwanted resorption of bone at the pressure site. In order to promote healing of bone fractures, the fracture surfaces that are brought together during reduction of the fracture should be subject to cyclic or periodic compressive forces so as to stimulate the growth of new bone across the fracture interface without causing bone resorption. When a fracture interface is immobilized, as by a cast, the bone material that is deposited at the fracture interface may have a collagen fiber matrix that is random rather than aligned with the fiber matrix of bone on either side of the fracture, the healed fracture interface being weaker in tension than bone on either side of the interface.

Some bone fractures result in the production of many bone fragments, and proper reduction of the fracture requires the fragments to be carefully reassembled next to each other with their fracture surfaces in contact. Bone screws and bone plate devices commonly are used for this purpose. Using bone screw techniques, two bone fragments may be joined together, and these two fragments as a unit may be moved into approximation with a third fragment and joined to it, and so on. Fragments that are thus joined together by rigid screws cannot move with respect to other fragments, and mismatching of the fracture surfaces as the first several fragments are joined together can have a compounding effect, causing malunion or non-union of fracture surfaces and resulting in far less than perfect bone fragment assembly and healing.

SUMMARY OF THE INVENTION

The invention involves an orthopedic fixation system for fixing a bone to an element which is a bone fragment or a prosthesis. The system includes a length of flexible, inelastic cord, a first fastener for attaching the cord to the element, a second fastener for fastening the cord to the bone, and optionally, a tubular support for placement along the cord. At least one of the fasteners has an opening through which the cord may pass from the interior of the bone to the exterior of the bone to enable the element to be securely mounted to the bone. The tubular support may be provided to prevent or reduce particulate shedding and ingrowth of bone into the cord to provide compressive resistance to the cable, or to deliver antibiotics or other pharmaceuticals.

In one embodiment, the invention involves a fracture relief system in which bone fragments are brought together by internal, inelastic flexible cords to counter forces tending to widen the fracture interfaces when the bone is stressed through normal, though often restricted, physical activity of a patient. Movement of fracture surfaces away from each other thus is prevented, but the flexible, inelastic cords do not restrict the transfer of compressive stress from one fragment to another fragment across fracture interfaces during physical activity. That is, the cords do not prevent the bone fragments forming a fracture interface from converging slightly to enable stress transfer. Due to their inelastic nature, the flexible cords do not maintain the fracture interface in compression during rest, and thus resorption of bone due to excessive constant compressive force is largely avoided.

The tubular support used with the invention may serve a variety of functions. The tubular support at least partially covers the cord of the invention to protect against particulate shedding. Further, the tubular support may prevent or reduce ingrowth of bone into the cord. Such prevention may be of particular importance where removal of the cord in the future is a possibility. A main function of the tubular support may be to provide compressive resistance. Such resistance may be especially advantageous in osteoporotic or weak bone or to compensate for bone loss. Temporary compressive resistance of the cord may be useful until new bone is formed and the material is gradually absorbed and replaced by normal bone (as with bioreabsorbable material). Using an elastic tubular support over an inelastic cord creates a fixation construct that is variable and treats a wide variety of fractures in cancellous and cortical bone. A further function of the tubular support may be to provide a medium for an antibiotic or pharmaceutical to be introduced. The antibiotic or pharmaceutical may be introduced into a matrix which allows diffusion of the antibiotic or pharmaceutical over time. This may aid in reduction of infection risk around the implant and damaged bone.

In another embodiment, the invention relates to a bone fracture reduction system for positioning bone fragments with respect to each other to reduce a fracture and promote healing. The system comprises a flexible, inelastic cord having an end portion, an optional tubular support for receiving the cord, a fastener attached to the end portion of the cord and adapted for attachment to a bone fragment in a direction generally coaxial to the axis of the end portion, and a second fastener attachable to the other bone fragment and having an opening through which the cord can be drawn to place the cord in tension. The second fastener includes a lock for locking the cord to the second fastener to restrain separation of the bone fragments.

In a further embodiment, the invention provides a bone fracture reduction system for reducing and promoting healing of a bone fracture. The fracture reduction system treats a fractured bone normally having an exterior cortical portion and a non-cortical interior, the bone having bone fragments with confronting fracture surfaces. An internal fastener is attached from within the bone interior to a first bone fragment with a length of flexible, inelastic cord extending within the bone interior and attached to said fastener and passing outwardly through an opening in a second bone fragment. A tubular support may be provided along the cord. The fastener and cord are so positioned as to draw respective fracture surfaces together to reduce the fracture upon tensioning of the cord extending outwardly through said opening. A second, external fastener desirably is attached to the bone opening, this fastener including an open bore to receive the cord and a lock to secure the cord to this fastener.

The invention also relates to a method for positioning fragments of a bone fracture with respect to each other to reduce the fracture and promote healing of a bone which normally has an exterior cortical portion and a non-cortical interior, the bone fragments having confronting fracture surfaces forming a fracture interface. The method comprises attaching from within the interior of the bone to a first bone fragment an internal fastener to which is attached a length of flexible, inelastic cord, and drawing the cord through an opening formed in a second bone fragment to draw the fragments together in a direction to reduce the fracture. The cord preferably is secured to the second bone fragment to maintain the bone fragments in a predetermined position to transfer compressive loads through the fracture interface during physical activity. Desirably, the method includes the step of determining the direction of tensile force desired to draw the fracture surfaces together, and positioning the cord approximately parallel to that direction. A tensioning instrument may be provided, the instrument having a first end portion grasping the cord that protrudes outwardly from the second bone fragment and a second end portion in contact with the external fastener, the method including the step of operating the instrument so as to separate the end portions and thus place the cord in tension to draw the bone fragments into the desired position.

A tubular support may be driven, as by pressure, along the insertion path of the cord. The distal end of the tubular support may be cut to conform to the surface of the first bone fragment. The proximal end of the tubular support may be configured for receiving a tool to rotate the tubular support, aiding in insertion, tightening, or removal. The tubular support may be a single support or may comprise a plurality or series of segments arranged end-to-end.

A plurality of internal fasteners may be fastened to different ones of a plurality of bone fragments, the internal fasteners having attached to them the length of flexible inelastic cord. The internal fasteners are so positioned with respect to each other that when the cord is tensioned, the bone fragments are drawn together in directions to properly join their respective fracture surfaces. As desired, one or more of the internal fasteners may include a pulley surface, such as that provided by an eyelet, over which the cord is movably trained to change the direction of the cord within the interior of the bone, the method including the step of pulling the cord over the pulley surface to tension the cord and properly position the bone fragments with respect to each other.

The flexible, inelastic cord system and methods of the invention may be employed to mount prosthetic devices to bone, such as acetabular cups to the acetabulum, bone plates to long bones, etc. Speaking broadly, a length of flexible, inelastic cord may be fastened at one end to a bone of a patient, the cord extending within the bone to a prosthesis which is to be held to the bone. For example, in the case of an acetabular cup, several cords may be employed that extend generally radially outwardly of the cup within the pelvis to maintain the acetabular cup in position.

DESCRIPTION OF THE PREFERRED EMBODIMENTS

As used herein, "cord" refers to any of a variety of materials that are strong in tension, inelastic, flexible, and biocompatible. If desired, the cord may be made of an organic suture material, or may be made from bioabsorbable materials such as poly (lactic acid). Preferably, however, the cord is made of a metal wire, such as in the form of a metal wire braid for improved flexibility. Stainless steel is an appropriate and preferred material. The cord is sufficiently flexible to substantially straighten within the bone interior when placed under sufficient tension to draw bone fragments together, that is, under a tension of about 5 or more newtons. The cord may be made of a single material or composite, or may include sections of different materials chosen for their particular properties such as strength, flexibility, and radiopacity to enable the cords to be readily visualized by fluoroscopy.

The cord of the present invention is sufficiently flexible as to exhibit substantially no axial compressive strength; that is, strength to resist axially applied compressive forces. The cord may be sufficiently stiff as to enable cord ends to be threaded through the eyelets of pulley-like fasteners and the like, but not sufficiently stiff to prevent bone fragments joined by a cord from converging, such prevention being the case with, for example, bone screws or rigid pins such as Steinman pins.

The cord is also generally inelastic. "Inelastic", as used herein, means that when a cord is placed in sufficient tension to draw bone fragments together, i.e., under tensile forces ranging generally from about 5 to about 800 newtons, the cord stretches elastically only a small amount if at all, so that the internal cord lengths extending from one bone fragment to another within a bone are under essentially no tension after the fragments have been properly anastomatized. Preferably, the cord demonstrates elastic recovery at body temperature of no more than about 10% upon release of a stretching force of 800 newtons.

As a result of the cord characteristics and use according to the present invention, the fracture interfaces are not stressed in compression by a cord when a patient is at rest, compression stress instead being applied intermittently through physical activity.

"Tubular supports" as used herein, refers to hollow cylinders or rods configured for receiving a cord therethrough. Preferably, the tubular support is manufactured of a material softer than bone and capable of accepting compressive stress without plastic deformation strain. Suitable materials are, for example, methyl methacrylate or polylactic acid. The tubular support may be threaded, may be smooth, or may alternately be threaded and smooth, as will be discussed in more detail below. In use, it may be desirable to provide a plurality or series of segments making up each tubular support, the segments having the same or varied lengths, to cover a portion of cord, thereby providing a flex pattern.

Figure 1:
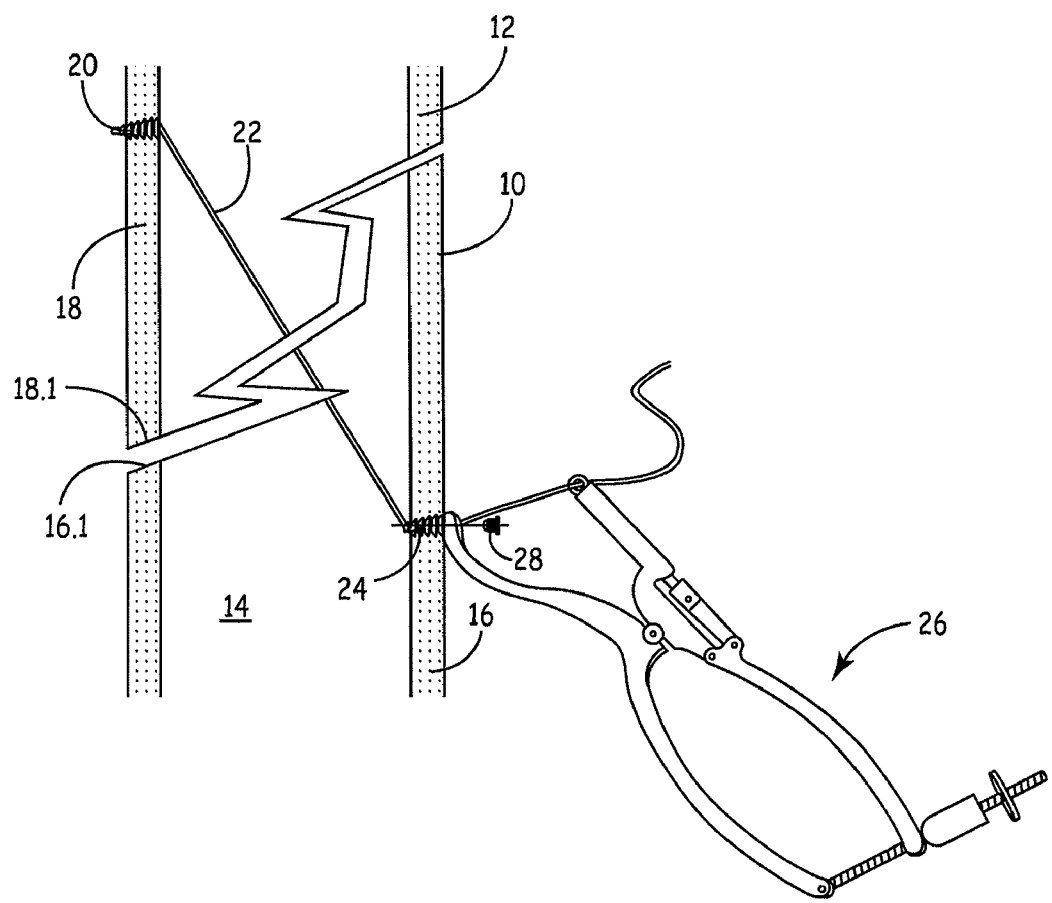
FIG. 1 is a partial cross sectional view of a fractured bone to which a cord fracture fixation device of the invention is being applied to reduce the fracture.

Referring first to FIG. 1, which illustrates a simple version of the invention, a fractured bone 10 is shown in schematic form as having an outer cortical portion 12 and an interior non-cortical portion 14. "Cortical" bone refers to the hard, dense, outer shell of a bone that bears stress in normal physical activities. The interior or non-cortical portion of some bones may simply be hollow, alternately, it may have interconnected trebeculae of cancellous bone. The cortical shell portion of bones typically ranges in thickness from about 2 mm to about 10 mm. The bone shown in FIG. 1 is broken into two bone fragments 16 and 18. The fracture surfaces of these bone fragments are shown at 16.1 and 18.1, respectively.

In the cortical bone portion 12 of fragment 18, there is placed a screw-type internal fastener 20, the designation "internal" referring to the fact that the fastener is attached to the bone fragment 18 from within the non-cortical interior of the bone. A flexible cord 22 attached to the fastener 20 extends across the interior of the bone as shown. Another screw-type fastener 24 is attached to the cortical portion of the other bone fragment 16. The fastener 24 may be termed an "external" fastener because it is attached to the bone fragment 16 from the exterior of the bone rather than the interior. The external fastener 24 has a hollow bore through which the cord 22 passes to the exterior of the bone. A hand-operated cord tensioning instrument 26, which bears against the fastener 24 and also which pulls the cord 22, may be used to tension the cord. A commercially available instrument of this type, commonly known as a Hall tensioning instrument, is described in Hall, U.S. Pat. No. 4,050,464, the teachings of which are incorporated herein by reference.

The internal and external fasteners 20 and 24 are positioned such that when the cord between them is placed in tension, the fracture surfaces 16.1 and 18.1 will be brought together at a fracture interface with the interface being maintained under compression as long as the cord 22 is maintained in tension. The external fastener 24 is provided with a locking device 28, preferably in the form of a screw, that is received in a threaded bore in the fastener 24 and which, in this embodiment, clenches the cord between the fastener 24 and locking device 28 to hold it in place. Other locking devices may, of course, be used. The tensioning instrument 26 is operated until the cord 22 between the fasteners 20 and 24 is straightened and the fracture surfaces of the fragments are properly joined. While moderate cord tension is maintained, the locking screw 28, or other locking device, is inserted, for example, in the fastener 24, to clamp the cord in place. Slight further movement of the fragments toward each other relieves the tension in the cord or cords, and the cord thereafter serves to prevent separation of the fracture surfaces as a patient engages in normal (although likely initially restricted) physical activity while freely permitting stress transfer across the fracture interfaces. Inasmuch as the newly formed bone at the fracture interface is subjected to stresses normally borne by that bone, the resulting collagen fiber matrix will have the correct alignment and provide a strong union between bone fragments.

A tubular support may be used with the cord fixation device of FIG. 1 to cover the cord, provide increased compressive resistance, prevent ingrowth of bone, provide a medium for introduction of an antibiotic or pharmaceutical, or for other use. Such tubular support is discussed in more detail in relation to FIGS. 15A-17B.

It is of importance to properly locate the fasteners 20 and 24 so that the resulting direction of the cord 22 is such as to reduce the fracture and maintain the bone fragments in the proper position for healing. A variety of devices and instruments may be employed to properly place the fasteners. The internal fastener 20 can generally be placed where needed because the fracture site itself is open and accessible to the surgeon.

The procedure for placing the cord fixation device of FIG. 1 involves the steps of gaining access from the interior of the bone to the desired position for the internal fastener 20, drilling a small pilot hole through the cortical bone at this location from the bone interior, providing the internal fastener 20 with cord attached, and threading the internal fastener 20 into the pilot hole, the internal fastener 20 cutting its own threads. If the site for the internal fastener 20 cannot be readily accessed, an access hole can be drilled into the opposite side of the bone across from the desired site and the site may be accessed through this hole with the cord being drawn downwardly (in FIG. 1) through the hole formed for the external fastener 24. Although the fasteners 20 and 24 in FIG. 1 and the fasteners described below are illustrated as having an elongated portion (threaded in FIG. 1) that extends approximately perpendicular to the surface of the bone, the fasteners may be attached at such other angles to the bone surface as may be appropriate to allow the force vector of the cord to parallel the axis of the fastener.

As described in greater detail below, a flexible, elongated tool may be used to reach into the bone interior to properly place the fastener. A guide wire may first be placed in the bone interior with the tip of the wire adjacent the position of the desired internal fastener. The elongated tool may have a hollow interior to enable it to slide over the guide wire and into the proper position, following which the tool may be operated to perform the needed drilling and fastener replacement procedures. Fluoroscopy may be employed to aid the surgeon in this procedure.

The surgical procedures involved in and use of the present invention are particularly beneficial for several reasons. Through careful placement of the fasteners, the desired force vectors may be obtained to pull two or more bone fragments together and affect proper union of their respective fracture surfaces. Further, placement of the fasteners is a fairly simple technique and does not require substantial tissue division or removal of supportive tissue (i.e., muscle, tendon) from a bone.

Figure 2:
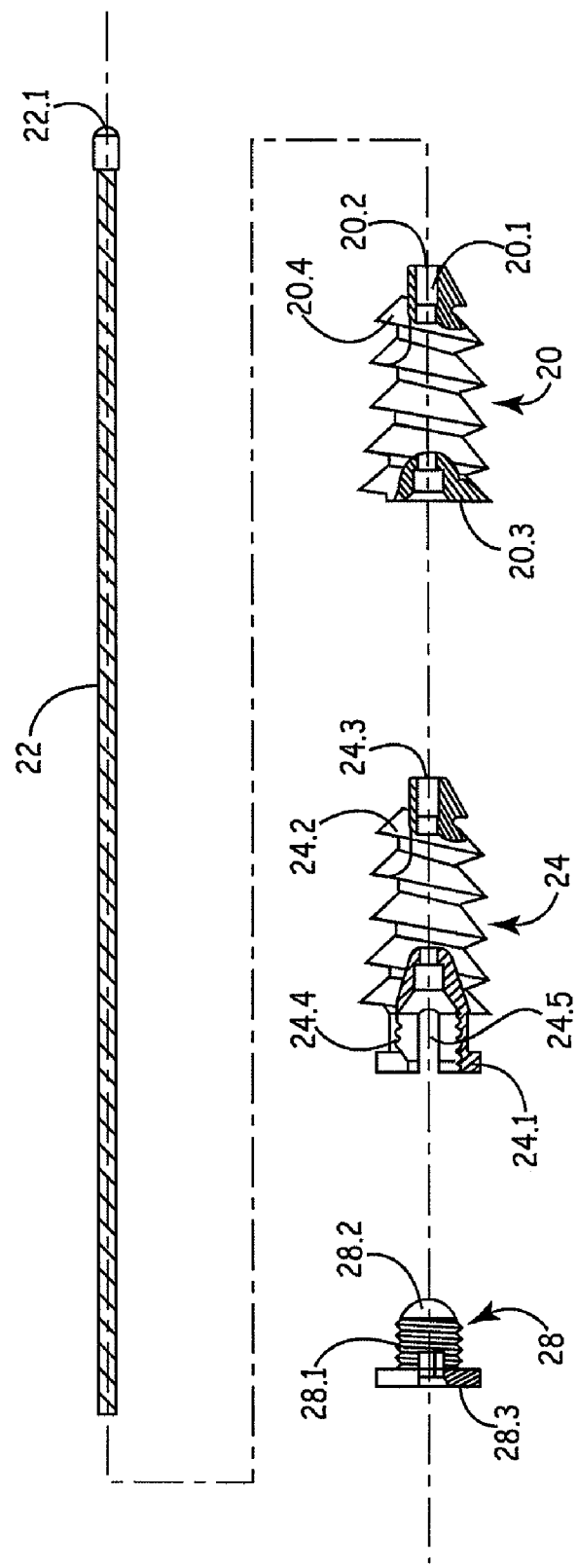
FIG. 2 is an exploded view, in partial cross section, of a device of the invention shown in FIG. 1.
Figure 3:
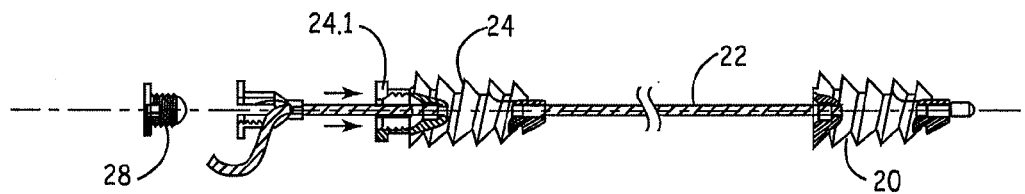
FIG. 3 is a partially exploded view, in partial cross section, of the device shown in FIG. 2.
Figure 7:
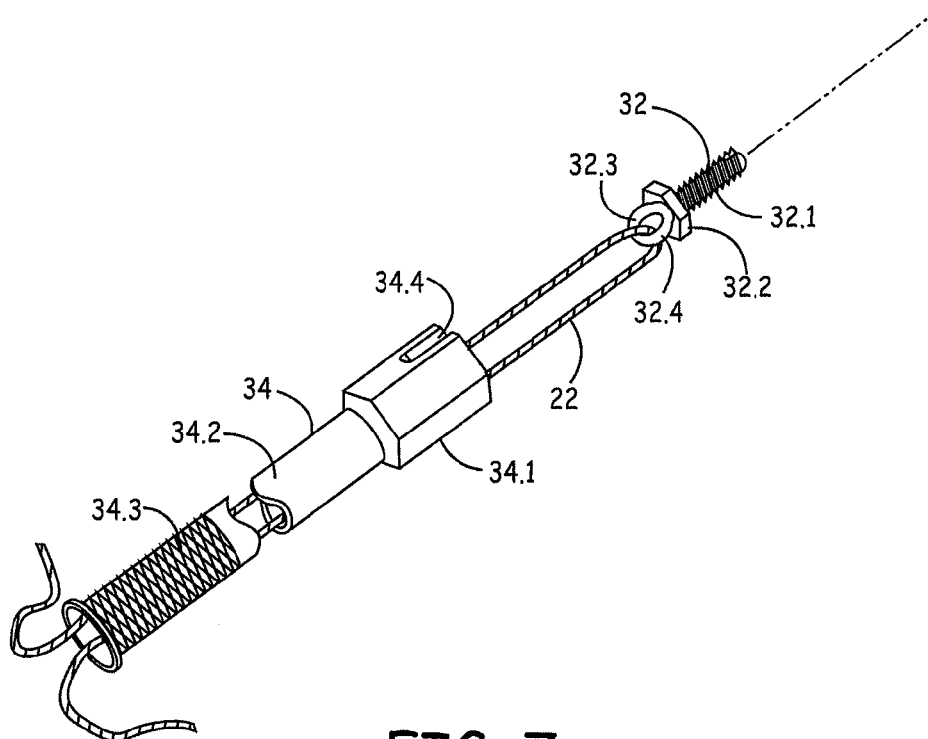
FIG. 7 is a perspective view, partially broken away, of a step in the installation of the pulley attachment element of FIG. 6A.

FIGS. 2 and 3 show the fastener and cord structure described above in connection with FIG. 1. The cord 22 may have an enlarged end portion 22.1 which may be a crimped-on sleeve, a welded-on collar, or other suitable structure. The cord 22 is inserted in a hollow bore 20.1 formed through the internal fastener 20, the enlarged end 22.1 of the cord 22 coming to rest within an enlarged distal end portion 20.2 of the bore 20.1. Preferably, the distal end portion 20.2 of the bore 20.1 has a spatial configuration complementary to the spatial configuration of the enlarged end portion 22.1 of the cord 22. The proximal end 20.3 of the internal fastener 20 is provided with an appropriate shape, such as a hexagonal perimeter or recess, to enable it to be turned by an appropriate tool such as a hollow, flexible nut driver as shown in FIG. 7 or an Allen wrench, or by some other means.

The internal fastener 20 desirably has self-cutting threads 20.4 of a design commonly utilized for bone screws. The cord 22 and the fasteners 20 and 24 must be sufficiently strong, of course, to bear the expected tensile stress to be placed on the cord 22. The external fastener 24 in FIGS. 2 through 5 has similar thread-cutting threads 24.2, and a generally hexagonal head or other appropriate shaped proximal end 24.1 to receive a tool such as the nut-driver of FIG. 7, the tool preferably having a hollow interior through which may pass the cord 22.

Figure 4:
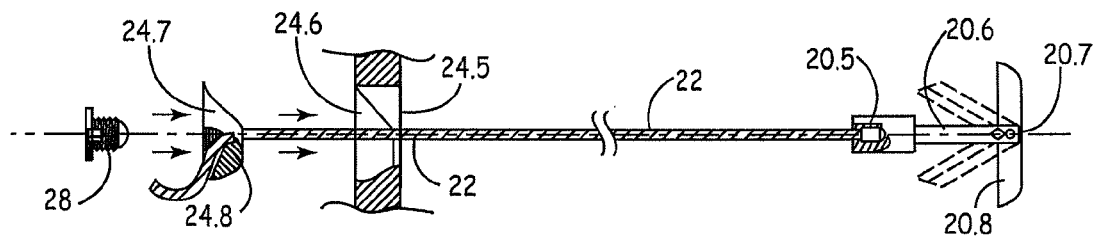
FIG. 4 is a partially exploded view, in partial cross section, of a modification of the device shown in FIG. 3.
Figure 5:
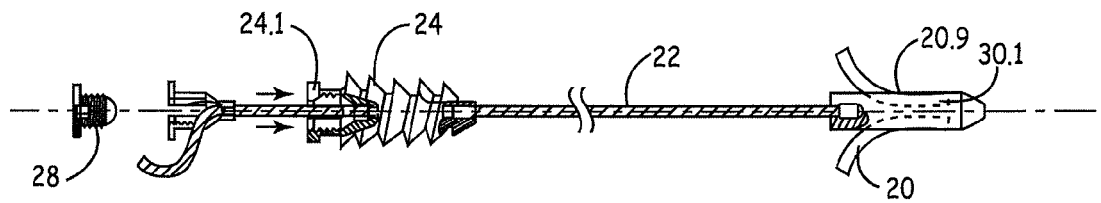
FIG. 5 is a partially exploded view, in partial cross section, of another modification of the device shown in FIG. 3.

As shown best in FIG. 2, the external fastener 24 has an interior bore 24.3 sized to slidingly receive the cord 22. At the proximal end of this fastener, the bore 24.3 has a widened, proximally open portion with interior threads 24.4 sized to threadingly receive the threads 28.1 of a locking screw 28. A different mechanism for locking the thread may, of course, be used wherein the proximally open portion of the fastener does not have interior threads 24.4. The threaded bore 24.4 has one or more, preferably four, circumferentially spaced, axially extending slots 24.5 that are sufficiently wide to permit the cable to pass into them as shown in FIGS. 3-5. The locking screw 28 is formed with a rounded distally facing nose 28.2 configured to come into contact with the cord 22 when the cord 22 extends through the slot 24.5, as shown in FIG. 3, the cord 22 being pinched between the nose 28.2 and the interior of the fastener 24 to lock the cord 22 in place. In the event that the cord 22 must be re-tensioned to adjust the position of a bone fragment, the locking screw 28 can be readily backed out from the fastener 24, the cord 22 re-tensioned as needed, and the locking screw 28 repositioned in the fastener 24.

Several different internal fasteners are shown in FIGS. 4 and 5. FIG. 4 illustrates an internal fastener 20.5 in the form of a toggle, the fastener 20.5 having an elongated, axially slotted shank 20.6 carrying at its distal end a pair of elongated arms 20.8 capable of swinging from the folded position shown in dashed lines in FIG. 4 to the fully extended position shown in solid lines in FIG. 4, the arms 20.8 being pivotally attached to the shank 20.6 by a pivot pin 20.7. In use, the internal fastener 20.5 is passed from the interior of the bone through a hole formed in a bone fragment until the arms 20.8 clear the hole, following which the arms 20.8 may move into the position shown in solid lines in FIG. 4 to contact the outer surface of the bone and thus anchoring the fastener 20.5 to the bone.

FIG. 4 also shows, as the external fastener, a dynamic compression plate 24.9 of known design, the plate 24.9 having a ramped orifice 24.6. Within the orifice 24.6 is received a complementary shaped insert 24.7 having an aperture 24.8 threaded to receive the locking screw 28. The cord 22 extends through the aperture 24.8, and the locking screw 28 locks the cord 22 to the insert 24.7.

Illustrated in FIG. 5 is an internal fastener 20.9 having a body carrying a pair of spring-loaded arms 30. The arms 30 are capable of being elastically pressed inwardly against the body 30.1 of the fastener 20.9 to enable the fastener 20.9 to be received through a bore formed in a bone fragment, the arms 30 springing outwardly into contact with the walls of the bore to anchor the fastener 20.9 in place. Alternately, various other fasteners of the types used to anchor sutures, such as the well known "fishhook" types, may be used.

Figure 6A:
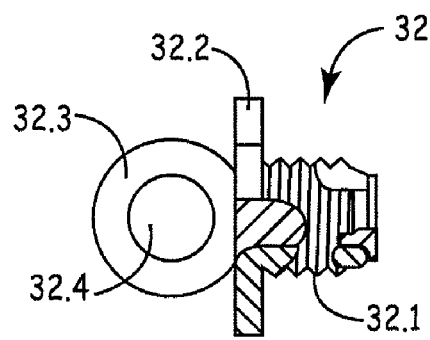
FIG. 6A is a view in partial cross section, of a fastener useful in the invention having a pulley surface.

As described in greater detail below, the internal fastener may have an internally extending eyelet or ring to provide a pulley-like surface over which the cord may be trained. With reference particularly to FIGS. 6A and 7, the fastener 32 is provided with a body 32.1 having self-tapping threads adapted to screw into cortical bone (into which is first preferably drilled a small pilot hole) and a hexagonal head 32.2. The fastener 32 includes a swivel body 32.3 that carries an eyelet 32.4 and that is attached to the threaded body 32.1 by means of a swivel mounting shown best in FIG. 6A. As illustrated, the threaded body 32.1 may have a hollow interior within which is rotatably mounted the swivel body with the latter having a flared end engaging the threaded body and preventing the swivel body from escaping.

Referring now to FIG. 7, a tool for mounting the threaded internal fasteners of the invention is shown generally at 34. The tool includes a distal end 34.1 having a hexagonally shaped recess to encounter the hexagonally shaped head portion of the fasteners, but Allen wrench configurations (in which the tool has a solid hexagonal end portion and the fastener head has a hexagonal recess) and various other tool/fastener shape configurations may be used as well. The tool includes an elongated body portion 34.2 and a handle portion 34.3 which may be conveniently knurled, as shown. Desirably, the tool is hollow so that a cord 22 can pass entirely through the tool, through the eyelet 32.4 of the fastener 32, and back through the handle 34.3 of the tool. In this fashion, when the tool is rotated about its axis to thread the threaded body 32.1 into cortical bone, the proximally extending eyelet 32.4 may remain substantially rotationally stationary to avoid twisting the cord 22. If desired, the distally open end 34.1 of the tool may have an axially extending, distally open slot such as that shown at 34.4 through which the cord 22 may extend when fasteners of the type shown in FIGS. 1-3 are threaded into bone. As mentioned above, the hollow interior of the tool may be employed to follow over a previously placed guide wire.

Figure 8A:
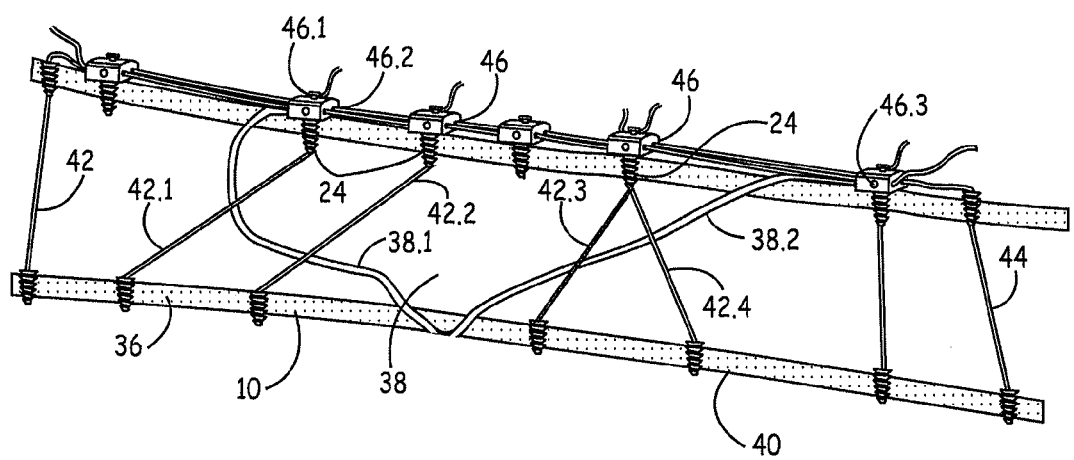
FIG. 8A is a partial cross sectional view of a fractured bone to which several cord fracture fixation devices are being applied to reduce the fracture.
Figure 8B:
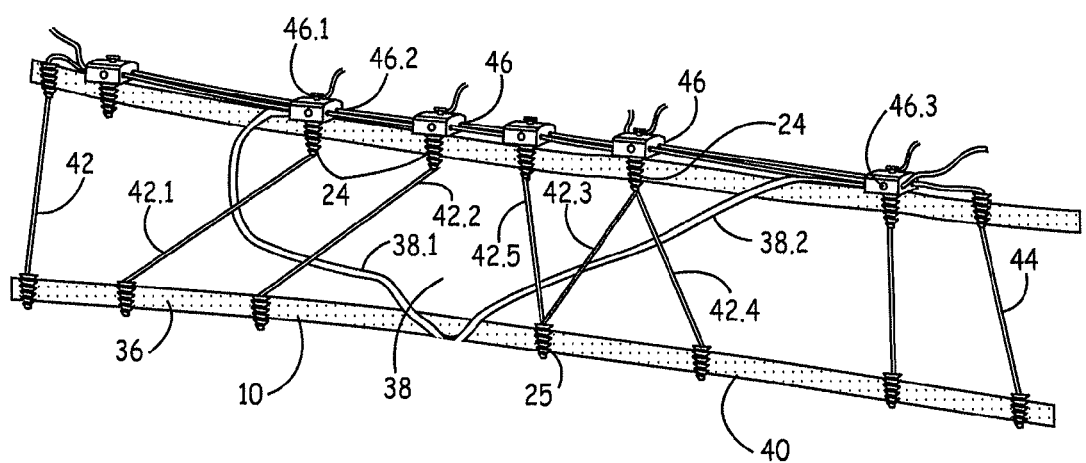
FIG. 8B is a partial cross sectional view of a fractured bone to which several cord fracture fixation devices are being applied to reduce the fracture.

FIGS. 8A-10 illustrate various ways in which the devices of the invention may be employed. Referring first to FIG. 8A, an elongated bone 10 is shown as having been broken into three bone fragments 36, 38 and 40. Cord systems of the type shown in FIGS. 1-3 are mounted at solid, unbroken end portions of the bones, the cords being shown as 42 and 44. A series of small bone plates 46, each having a curved bottom surface to fit against the exterior of the bone, are provided. Each of the bone plates 46 has a central bore 46.1 for receiving an external fastener 24 and has one or more bores 46.2 extending within the bone plate 46 generally parallel to the axis of the bone and capable of slidably receiving the cords 42 and 44. One fracture 38.1 is reduced through the use of the cords 42.1 and 42.2, and the other fracture 38.2 is reduced through the use of cords 42.3 and 42.4. Note that two of the cords 42.3 and 42.4 each have proximal ends passing through a single external fastener 24. The cords 42 and 44 extend laterally through the bores 46.2 in the bone plates 46, the cords 42 and 44 being appropriately manipulated to properly bring together the fracture surfaces of the bone fragments. FIG. 8B illustrates a slight variation of FIG. 8A wherein a further cord, cord 42.5 is used in conjunction with cords 42.3 and 42.4 to reduce the fracture 38.2. Two of the cords 42.3 and 42.5, have distal ends extending through a single internal fastener 25. Cords 42 and 44 may be locked to the endmost bone plates and to such other plates as may be desired through use of such locking devices as are typified in FIGS. 11A-11C; that is, a threaded bore, such as that designated as 56.7 in these figures, may be formed in the bone plates 46 of FIG. 8 at an angle to and intersecting the cord-receiving bores 46.2. A set screw 46.3 or the like may be threaded into the threaded bore to engage the cord and lock it to the plate.

Figure 6B:
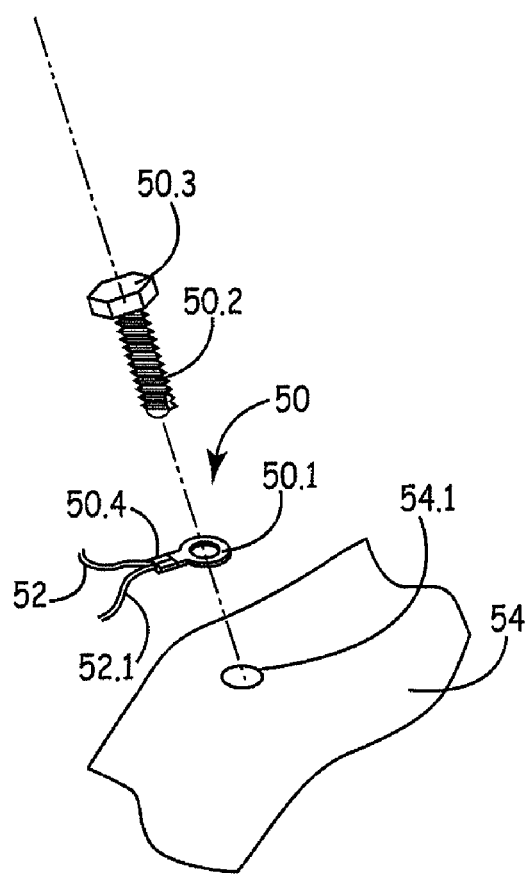
FIG. 6B is an exploded view of another fastener useful in the invention.
Figure 9A:
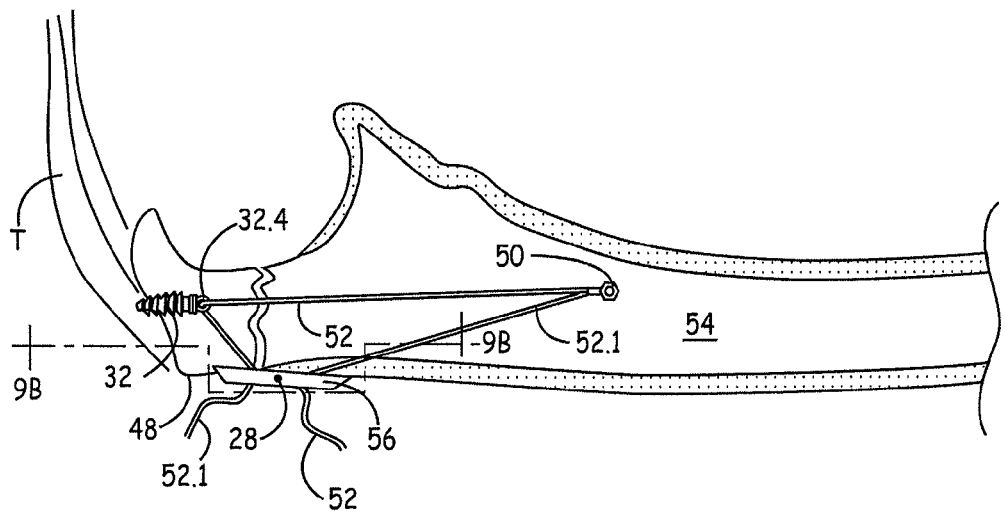
FIG. 9A is a broken away cross sectional view of an elbow olecranon fracture to which a fracture fixation device of the invention is being applied.
Figure 9B:
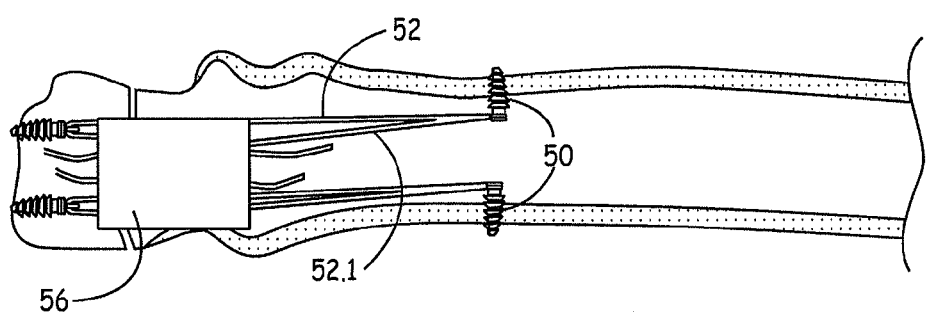
FIG. 9B is a broken-away, cross sectional view taken along line 9B-9B of FIG. 9A.

FIGS. 9A and 9B show the reduction of an olecranon fracture of the type that might result from trauma to the ulna by a fall on the outstretched hand, the fracture most commonly resulting from the severely tensioned triceps. It is important to reduce the fracture by drawing the bone fragments together and maintaining the fragments in proper alignment during healing, the fracture interface resisting separation under the force of the triceps. An internal fastener 32 of the type shown in FIGS. 6A and 7 is placed from within the interior of the bone into the bone fragment 48, as shown in FIG. 9A. A second internal fastener 50 is placed distally from the fracture site within the ulna, as shown in the drawing, the vector between the fasteners 32 and 50 denoting the direction of the resulting tensile forces that will be placed on the cord 52 extending between them. The second internal fastener 50 may, if desired, include a pulley surface of the type provided by the eyelet 32.4 of the internal fastener 32 in FIG. 9A, or may be of a different design such as the type shown in FIG. 6B. As seen in FIG. 6B, the fastener comprises a ring 50.1 to be received against the surface of the bone 54, and a bone screw 50.2 having a ring-contacting wide head such as the hexagonal head shown at 50.3, the threaded portion of the screw 50.2 being sized to pass through the ring 50.1 and into a pilot hole 54.1 formed in the bone to securely fasten the internal fastener 50 to the bone. Cords 52 and 52.1 are attached to the fastener by a crimp such as shown at 50.4 or by other means.

Fractures of such bones as the olecranon and the patella may result from extremely high tensile forces that are generated, in the case of the olecranon, by the triceps muscle, and, in the case of the patella, by the quadriceps muscle group. Reduction of fractures in these bones in the past has been accomplished through the use of external wires in what has become known as a "figure of eight" technique, the wires being trained around the ends of pins protruding from the bone fragments and the wires themselves laying against the outer bone surface. This external fixation technique has many of the drawbacks associated with cerclage techniques in that placement of the wires requires exposure of substantial exterior bone surface areas with associated loss of connective and supportive tissue. The use of extensive external wire structures can be largely avoided or eliminated in accordance with the present invention.

Referring again to FIG. 9A, the cord 52 extends from the second internal fastener 50 through the eyelet 32.4 of the internal fastener 32 and thence out through an opening formed in the bone. If desired, the second internal fastener 50 may be attached by utilizing screw fasteners having self-drilling and self-tapering screw portions, as shown in FIG. 7. An elongated tool having a right-angled drill adapter can be employed to attach the fastener to the bone. The cord 52.1 similarly is drawn out through the opening formed in the bone. An external fastener of the type described in connection with FIGS. 1-3 may be employed at the opening of the bone, the cords 52 and 52.1 passing outwardly through the fastener. After suitable tension has been applied to the cords 52 and 52.1, the cords 52 and 52.1 may be secured to the fastener in the manner described above. If desired, the external fastener may include a bone plate 56 as shown. Preferably, two generally parallel but transversely spaced cord systems are employed, as shown in FIG. 9B.

As the cord 52 is tensioned, the bone fragment 48 is pulled to the right into contact with the ulna to reduce the fracture. The internal fastener 32 acts as a pulley; as the externally extending portion of cord 52 is pulled, some mechanical advantage is obtained to reduce the fracture. If desired, only the cord 52 need be employed in this procedure to reduce the fracture and to maintain the fracture interface in position. In this event, the cord 52 will exert force on the bone plate 56 in the direction of the internal fastener 32, and the cord 52.1 may be employed to provide a counteracting, substantially balancing force vector. It will be noted that the cords 52 and 52.1 together are positioned to counter the force exerted by the triceps, shown as T in FIG. 9A.

Figure 11A:
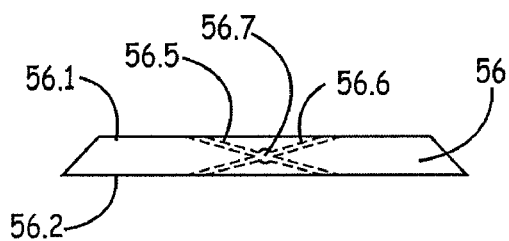
FIG. 11A is a side view of a bone plate shown also in FIGS. 9A and 9B.
Figure 11B:
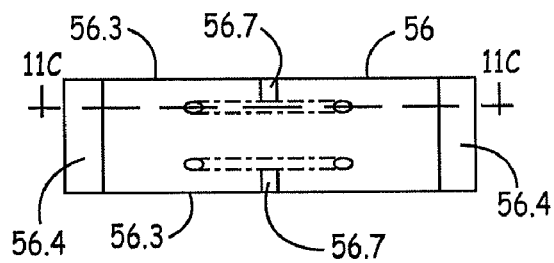
FIG. 11B is a top view of the plate of FIG. 11A.
Figure 11C:
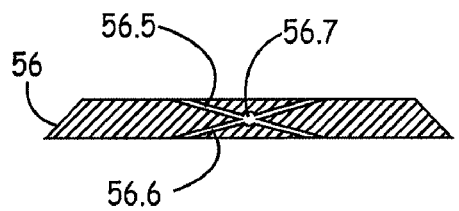
FIG. 11C is a cross sectional view taken along line 11C-11C of FIG. 11B.

The bone plate 56 shown in FIGS. 9A and 9B is illustrated in greater detail in FIGS. 11A, 11B and 11C. The bone plate 56 may be made of plastic or steel or other biocompatible, rigid material and includes a top wall 56.1, and a bottom wall 56.2 which is slightly concave in order to fit more closely the convex surface of bone such as the ulna as shown in FIGS. 9A and 9B, side walls 56.3 and end walls 56.4, the end walls being tapered to avoid trauma to overlying soft tissue. Cord-receiving bores 56.5 and 56.6 are formed at an acute angle to the top and bottom walls 56.1 and 56.2, as illustrated best in FIGS. 11A and 11C. These bores 56.5 and 56.6 intersect intermediate the top and bottom walls, and threaded bores 56.7 are formed in the side walls 56.3 and extend toward each other so as to intersect the bores 56.5 and 56.6 at their point of intersection. The threaded bores 56.7 are so oriented as to receive a set screw (not shown) which, when fully inserted, engages cords passing through the bores 56.5 and 56.6 to lock them in place.

Figure 10:
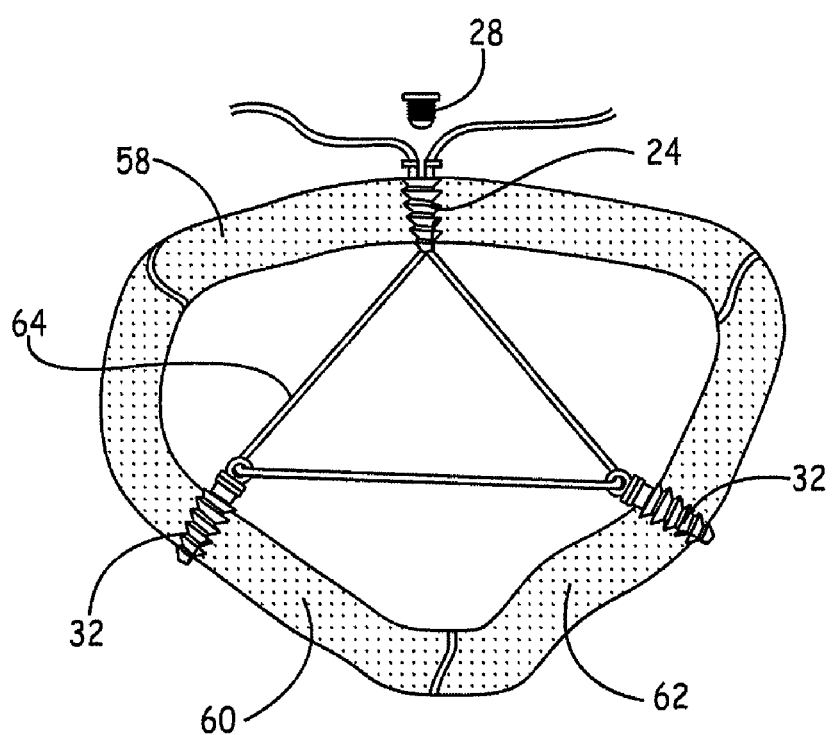
FIG. 10 is an end-on cross sectional view of a fractured bone to which a fracture fixation device of the invention has been applied.

FIG. 10 illustrates the use of pulley-like fasteners 32 within a bone. This figure shows a bone end-on, the bone having been broken into three fragments 58, 60 and 62. Internal fasteners of the type shown at 32 in FIGS. 6A and 7 are placed from the interior of the bone into each of bone fragments 60 and 62 with the cord 64 extending through the pulley-like eyelets of the fasteners 32. Both ends of the cord 64 are drawn out of the bone through an external fastener 24 of the type shown in FIGS. 1-3, the latter being carried by bone fragment 58. The internal fasteners 32 and the external fastener 24 are so positioned that when the ends of the cord 64 that extend outwardly through the external fastener 24 are placed in tension and are secured to the external fastener 24 through the locking screw 28, the fragments are urged together to properly reduce the fracture and to prevent the fracture surfaces from separating. The pulley surfaces of the fasteners 32 enable slight movement of the cord 64 as stress is applied, thereby balancing any tensile forces in the cords and avoiding unwanted shifting of one bone fragment with respect to another due to unequal loading.

Note also in connection with FIG. 10 that the vector of the resultant force applied to each bone fragment is not parallel to the direction of the cord 64, but rather depends for each fragment upon the angle between the cord segments leading to that fragment and the tension in each cord segment. Assuming that the tension in each of the three cord segments fracture reduction occurs is approximately the same, the vector of the resultant force acting on each fastener approximately bisects the angle between the cord segments leading to that fastener, and knowledge of this relationship may aid the surgeon in proper placement of the fasteners.

Figure 12A:
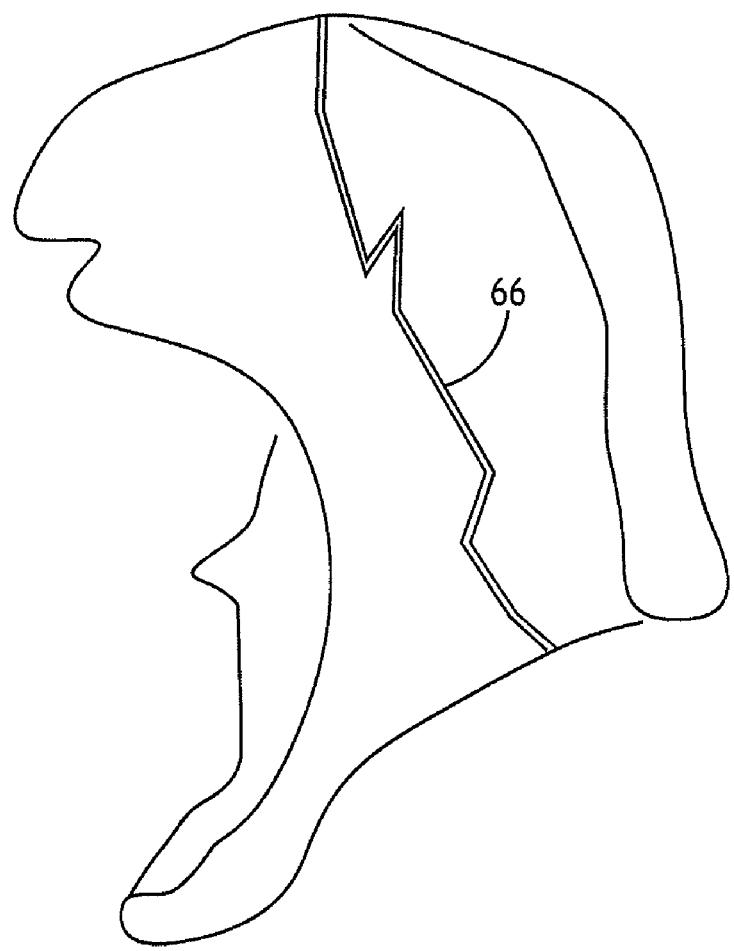
FIG. 12A is a schematic representation of the pelvis, showing the location of a fracture in the ilium to be reduced by a method of the invention.
Figure 12B:
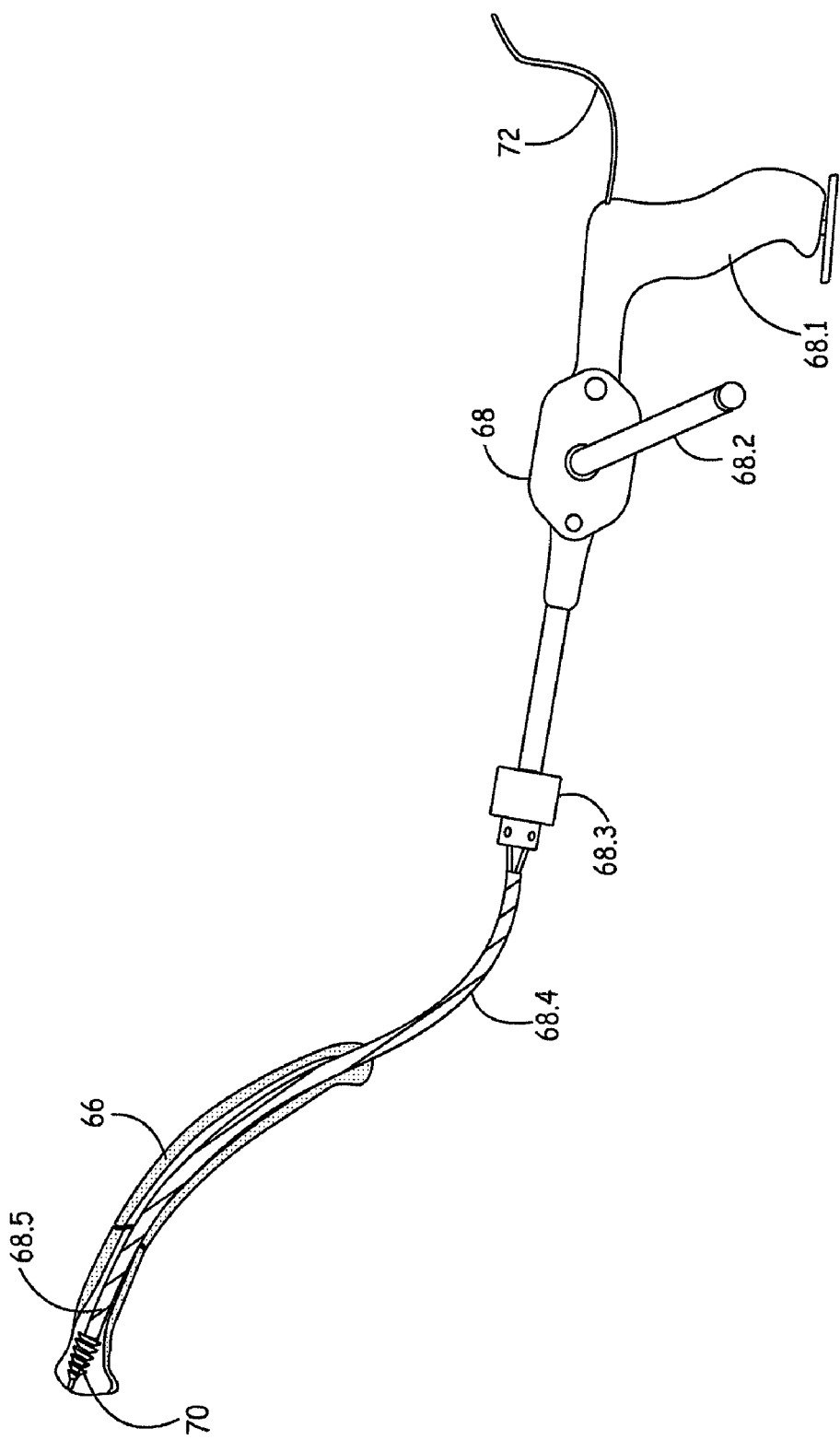
FIG. 12B is a cross sectional view of the pelvis of FIG. 12A showing a step in the reduction of the fracture.
Figure 12C:
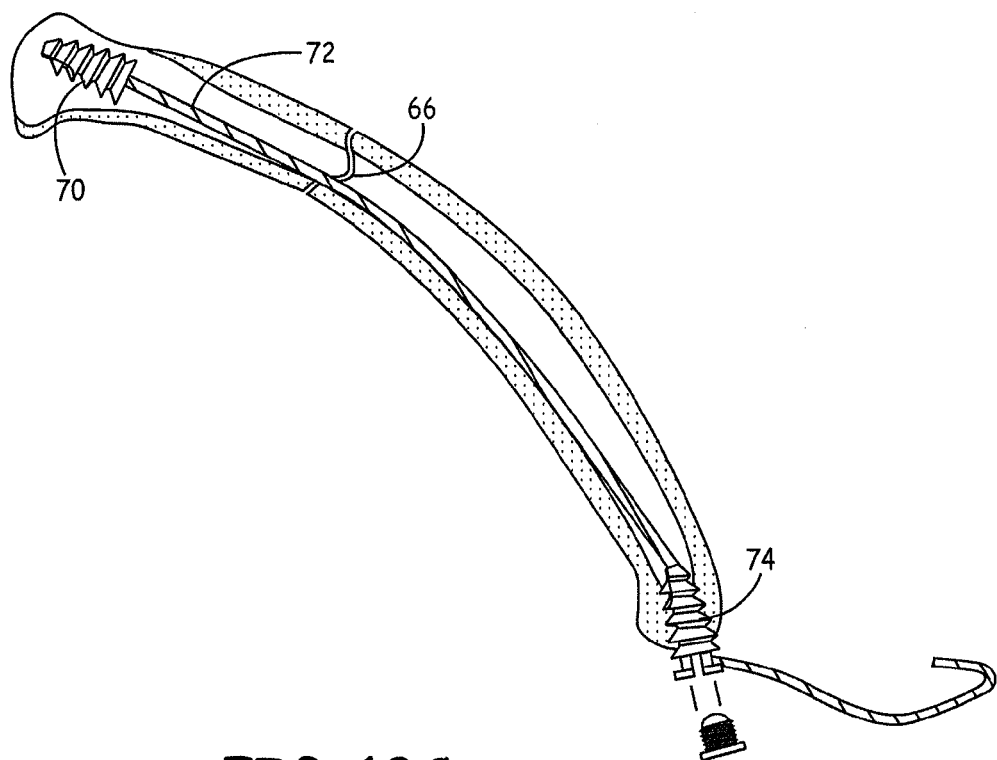
FIG. 12C is a cross sectional view of the pelvis of FIG. 12A showing the reduced bone.

FIGS. 12A, 12B and 12C show steps in the reduction of a fracture of the ilium of the pelvis, the fracture being designated generally as 66. FIGS. 15B and C, discussed further below, mirror FIGS. 12B and 12C, but include a tubular support with the cord fracture fixation device. It is desired here to run a flexible, inelastic cord 72 from within the pelvis to cortical bone on the far side of the fracture, fastening the cord 72 to the cortical bone, the cord 72 thus running past the fracture site and exiting the pelvis on the near side of the fracture site. Referring to FIG. 12B, installation of the cord 68.4 and internal fastener 70 is facilitated through the use of an external drill 68, the external drill 68 comprising a hand grip 68.1, a rotatable handle 68.2, a chuck 68.3, and a gear mechanism (not shown) that causes the chuck to rotate about its axis in response to rotation of the handle 68.2. The drill 68 may be of the type marketed by DePuy as its Modified Pease Bone Drill, Model 2079-00. A flexible cable 68.4 is provided, the cable being of known design and torsionally stiff so that rotation of the cable 68.4 at its end where attached to the chuck 68.3 results in rotation of the cable 68.4 at its distal end 68.5. An internal fastener of the type shown in FIG. 3 is shown at 70, and is provided with a hexagonal head which is inserted within a hexagonal end of the flexible cable 68.4 such that as the cable 68.4 is rotated about its axis, the threaded fastener 70 is threaded into cortical bone with the cord (not shown) extending from the fastener through the hollow interior of the flexible cable 68.4 such that when the fastener 70 has been suitably fastened to cortical bone, the flexible cable 68.4 can be withdrawn from the pelvis leaving behind it the flexible, inelastic cord within the bone.

The cord in FIG. 12C is designated 72, and extends from the internal fastener 70 across the fracture 66, around the bends in the ilium, and exits the pelvis through an external fastener of the type described above and designated 74. Although only one such cord is shown in the figure, a plurality of such cords, extending in the necessary directions to reduce the fracture, may be employed. The cord 72 is placed under tension to reduce the fracture and is secured in the external fastener 74 in the manner described above to prevent the fracture interface from reopening.

Figure 13A:
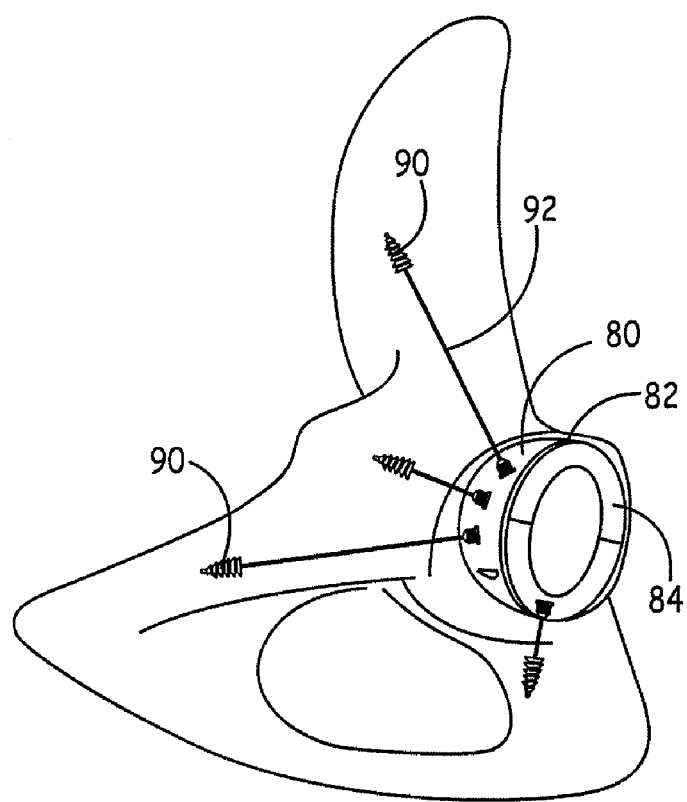
FIG. 13A is a schematic perspective view of a portion of the pelvis showing an acetabular cup prosthesis held in position by a cord system of the invention.
Figure 13B:
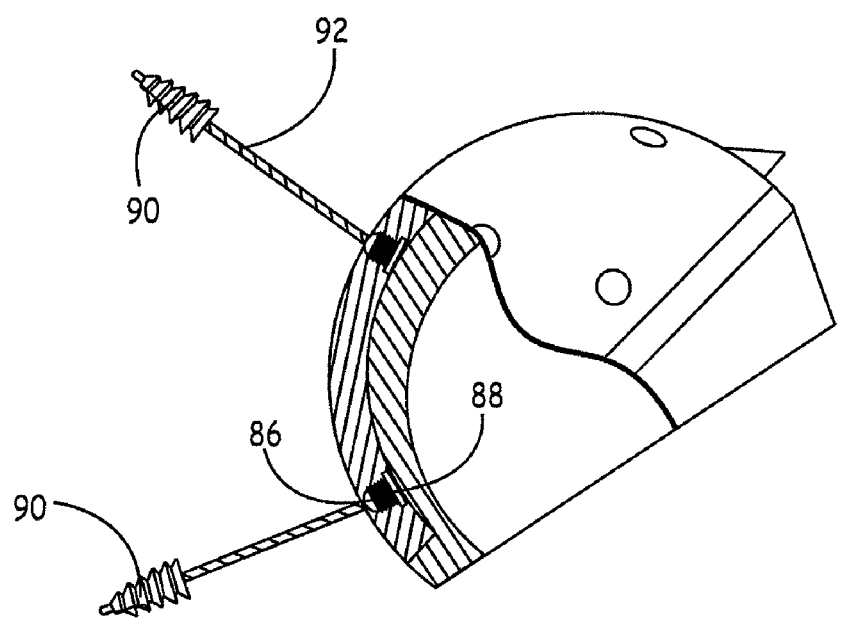
FIG. 13B is a partially broken away side view of the prosthesis shown in FIG. 13A.

FIG. 13A shows use of the cord system of the invention for fixation of a prosthetic acetabular cup to the acetabulum of a patient. Designated 80 in FIG. 13A is a prosthetic acetabular cup, commonly comprising a cup-shaped jacket 82 formed of titanium or other biocompatible metal, and an inner cup 84 having a generally hemispherical cavity in it to receive the ball of the femur. The outer surface of the jacket 82 may have threads or spikes or other surface configurations enabling it to grip tightly to the bony acetabulum once the latter has been surgically shaped to receive the prosthesis. An adhesive may be applied to the jacket 82 or the acetabulum to ensure fixation of the jacket 82 in the acetabulum. In accordance with the invention, the generally cup-shaped jacket 82 is provided with a series of apertures 86 (FIG. 13B) which may be threaded to receive lock nuts 88, the threaded apertures 86 and lock nuts 88 themselves forming an external fastener as generally referred to above. Internal fasteners 90 are attached from within the pelvic bone to the cortical bone thereof in the manner described above in connection with FIGS. 12B and 12C, the flexible, inelastic cords 92 extending within the pelvis back through the apertures 86 in the acetabular cup 80. Desirably, three, four, or more, such cords 92 are employed, extending preferably generally radially outwardly from the acetabular cup 80 in a variety of different directions. The ends of the cords 92 are individually suitably tensioned to properly position the acetabular cup 80, the ends of the cords 92 extending into the jacket 82 then being locked in place through the use of the locking screws 88. The polymeric inner cup 84 is then placed in the jacket 82. The purpose of the flexible, inelastic cords 92 is to hold the acetabular cup 80 in place and, as needed, to repair fractures in the pelvis.

Figure 16A:
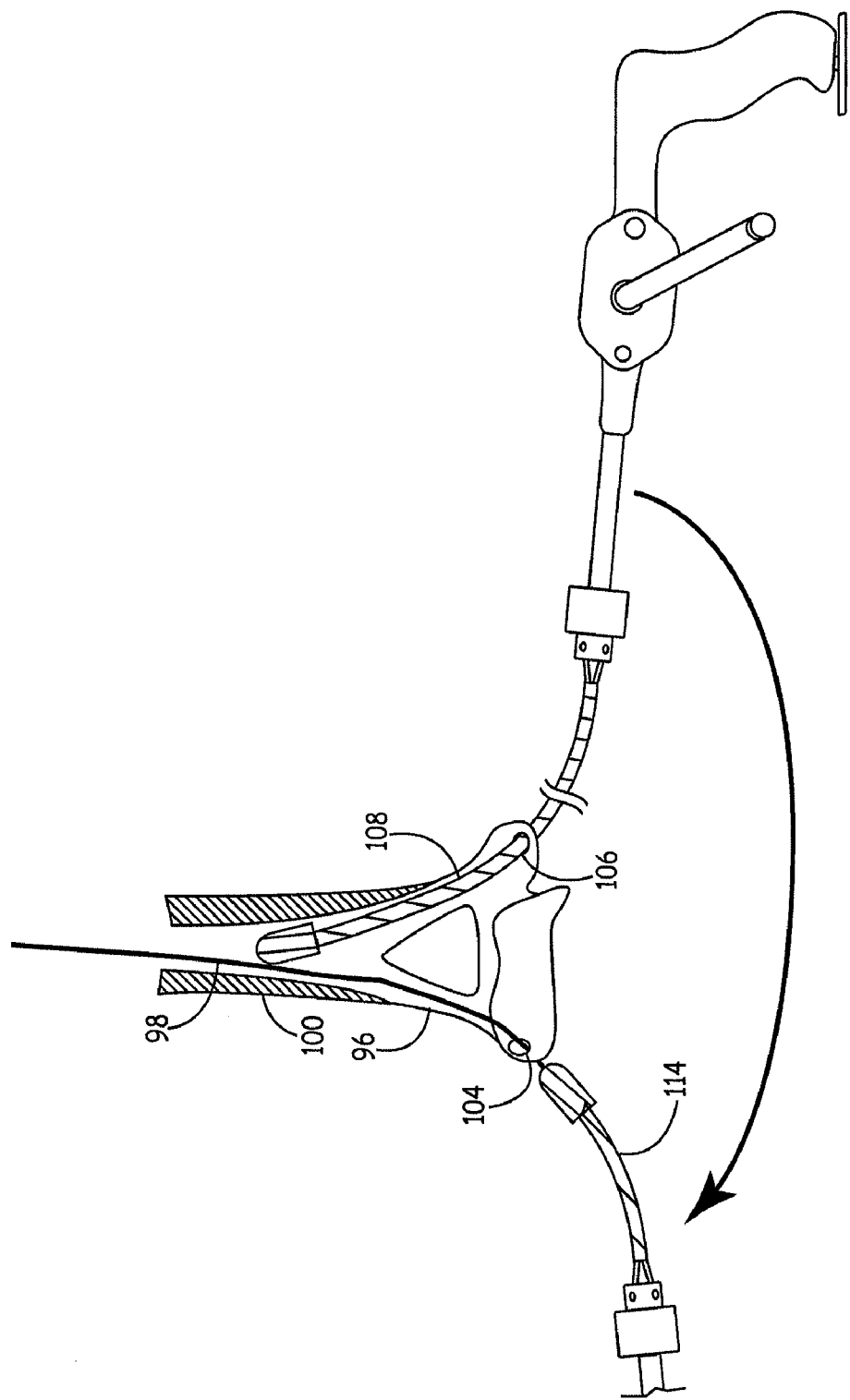
FIG. 16A is a schematic representation of the distal end portion of the humerus showing a step in the placement of a cord system of the invention.

Referring now to FIGS. 14A-D and 14F, these figures depict how the flexible, inelastic cords of the invention may be used to reduce fracture of a long bone such as the humerus. FIG. 16A, discussed below, mirrors FIG. 14A, but includes a tubular support with the cord fracture fixation device. A fractured humerus is designated 96 and includes a medullary canal 98 bounded by cortical bone 100. The fracture site is shown best in FIGS. 14D and 14F, the fracture interfaces being designated 102. At its distal end, on either side of the olecranon, the humerus has thin walled portions through which are drilled holes 104 and 106 for introduction of a cord system of the invention.

Figure 14A:
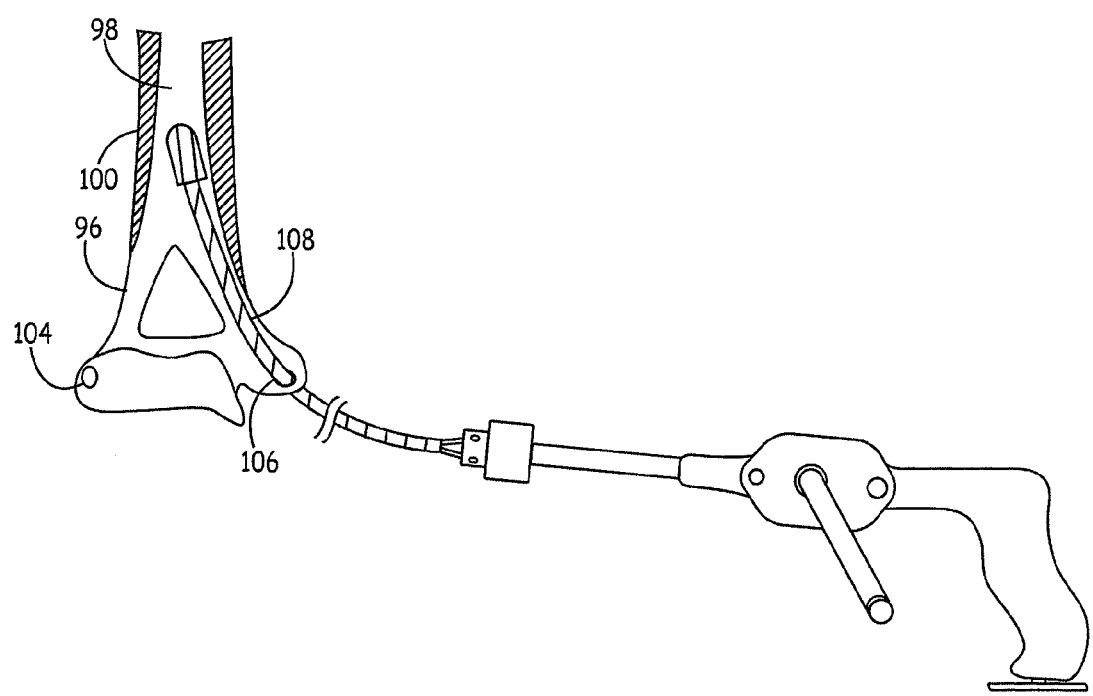
FIGS. 14A, B and C are schematic representations of the distal end portion of the humerus showing different steps in the placement of a cord system of the invention.
Figure 14B:
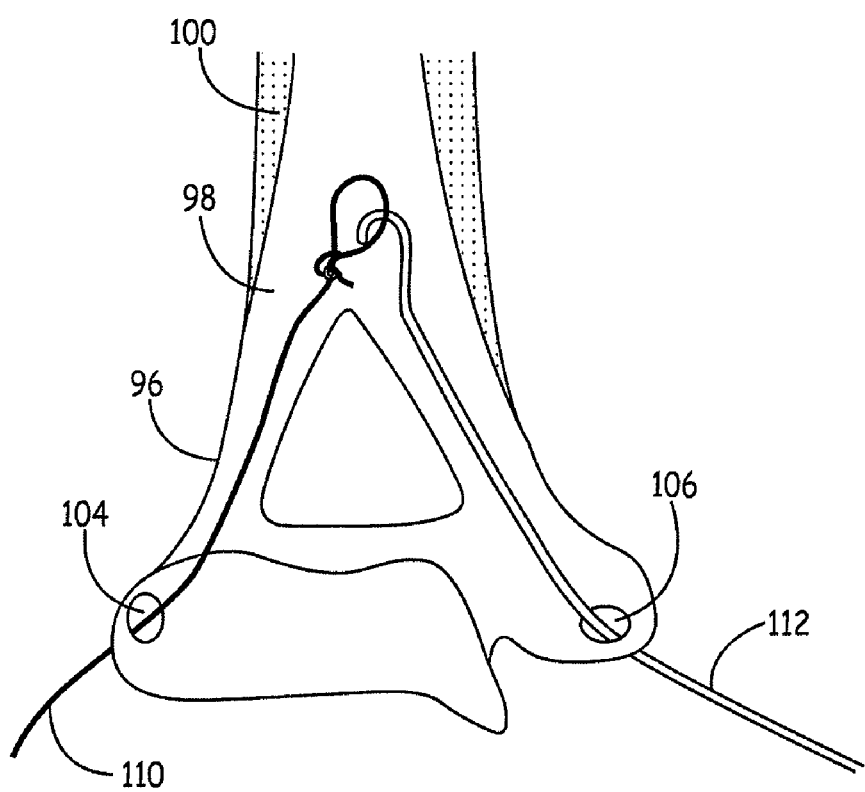
FIG. 14D shows a toggle type cord fixation system employed in the humerus mounted on a flexible installation rod and shown during insertion of the toggle.
FIG. 14E is a perspective view of a toggle of the type shown also in FIG. 14D.
FIG. 14F is a schematic view, in partial cross section, of the humerus showing a fracture relieved through the use of the toggle and cords shown in FIGS. 14A-14E.
Figure 14C:
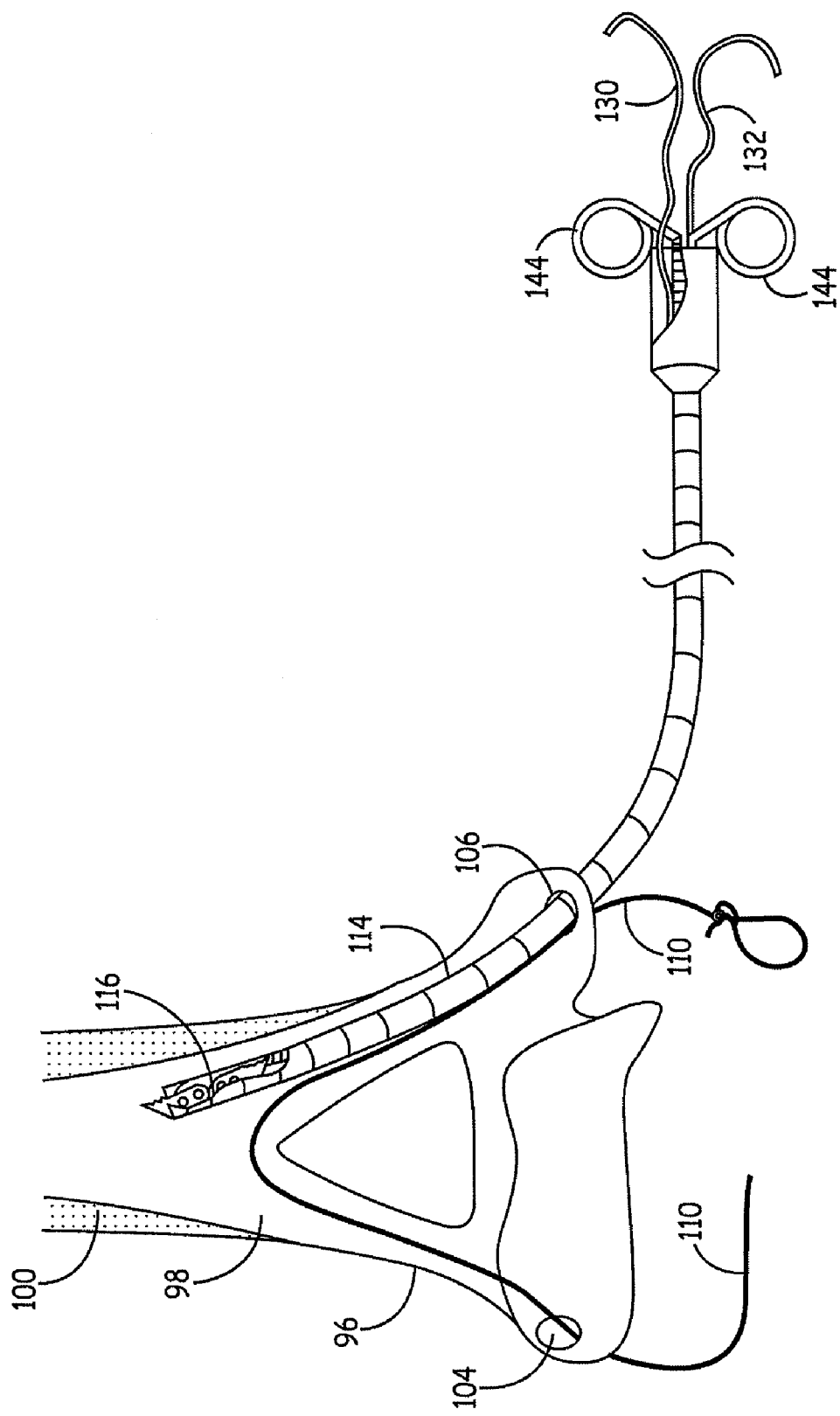

The holes 104 and 106 may be formed through the use of a drill of the type described above, such as in reference to FIG. 12B the drill having a flexible shaft shown schematically as 108 in FIG. 14A. The elongated bores formed by the drill 108 converge at a point spaced proximally from the olecranon, and further movement of the flexible drill shaft upwardly (proximally) within the medullary canal 98 serves to remove some of the tissue in the canal to make way for the cord system. It is desired, once the cord system is in place, that a pair of spaced cords traverse the fracture site within the medullary canal, each cord exiting at one of the holes 104 and 106. For ease in placement of the cord system, each of the cords may initially exit through hole 106, with one of the cords thereafter being drawn downwardly through hole 104. This may be accomplished as shown in FIGS. 14B and 14C. A wire 110 having a loop at one end is inserted through the hole 104, the loop then being snared by a hook-shaped end of a snare wire 112 that is inserted through the other hole 106. The snare wire 112 then can be removed and discarded.

Figure 16B:
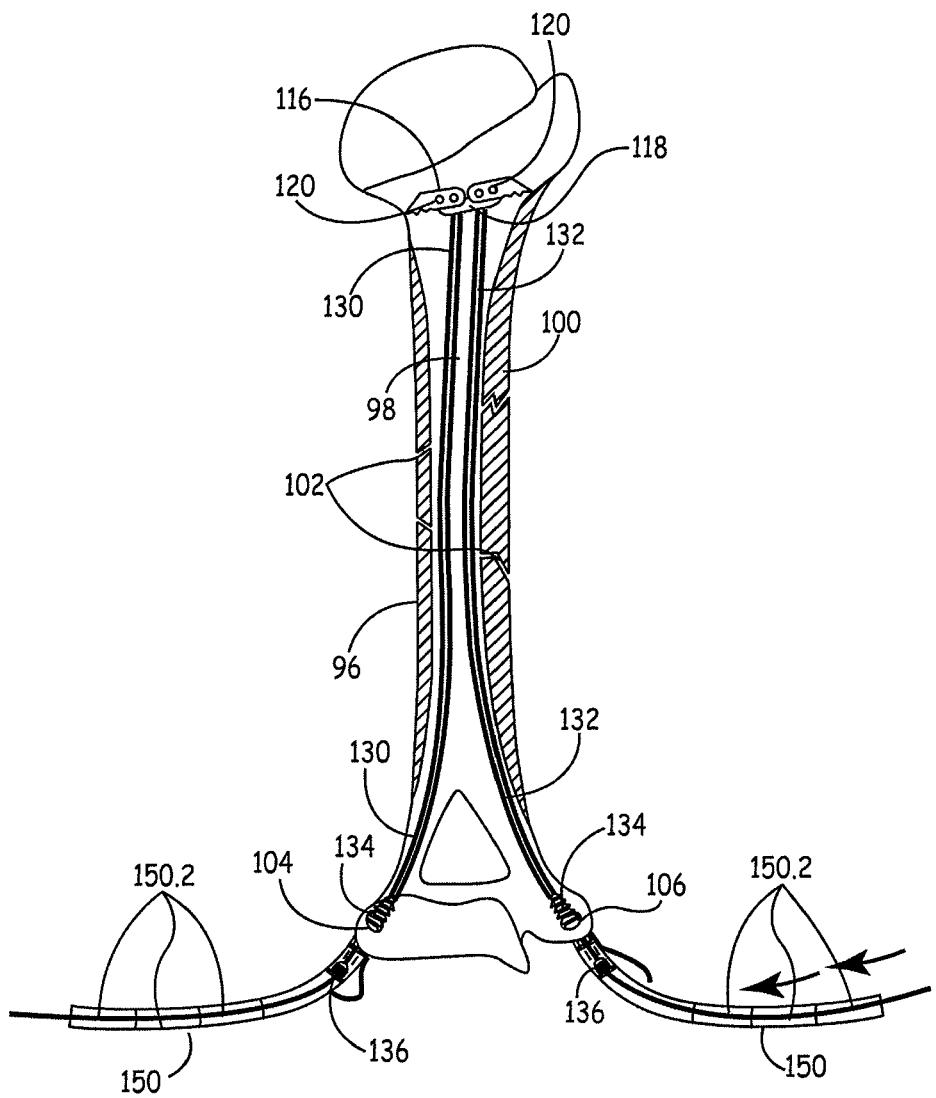
FIG. 16B is a schematic view, in partial cross section, of the humerus showing a fracture relieved through the use of the toggle and cords shown in FIGS. 14A-14E and the tubular support shown in FIG. 16A.

Through the hole 106 is introduced a flexible, hollow introducer tube 114 carrying within it a toggle 116, the toggle 116 being of the type shown best in FIGS. 14C through 14F. FIG. 16B, discussed below, mirrors FIG. 14F, but includes a tubular support with the cord fracture fixation device. Turning to FIGS. 14C-14F, the toggle 116 is shown as having an extended orientation in which it is received in the tube 114 (FIG. 14C) and in which it is eventually deployed in the medullary canal (FIG. 14F), and an articulated orientation (FIG. 14F) permitting it to be moved within the close confines of the medullary canal during placement of the toggle.

Figure 14D:
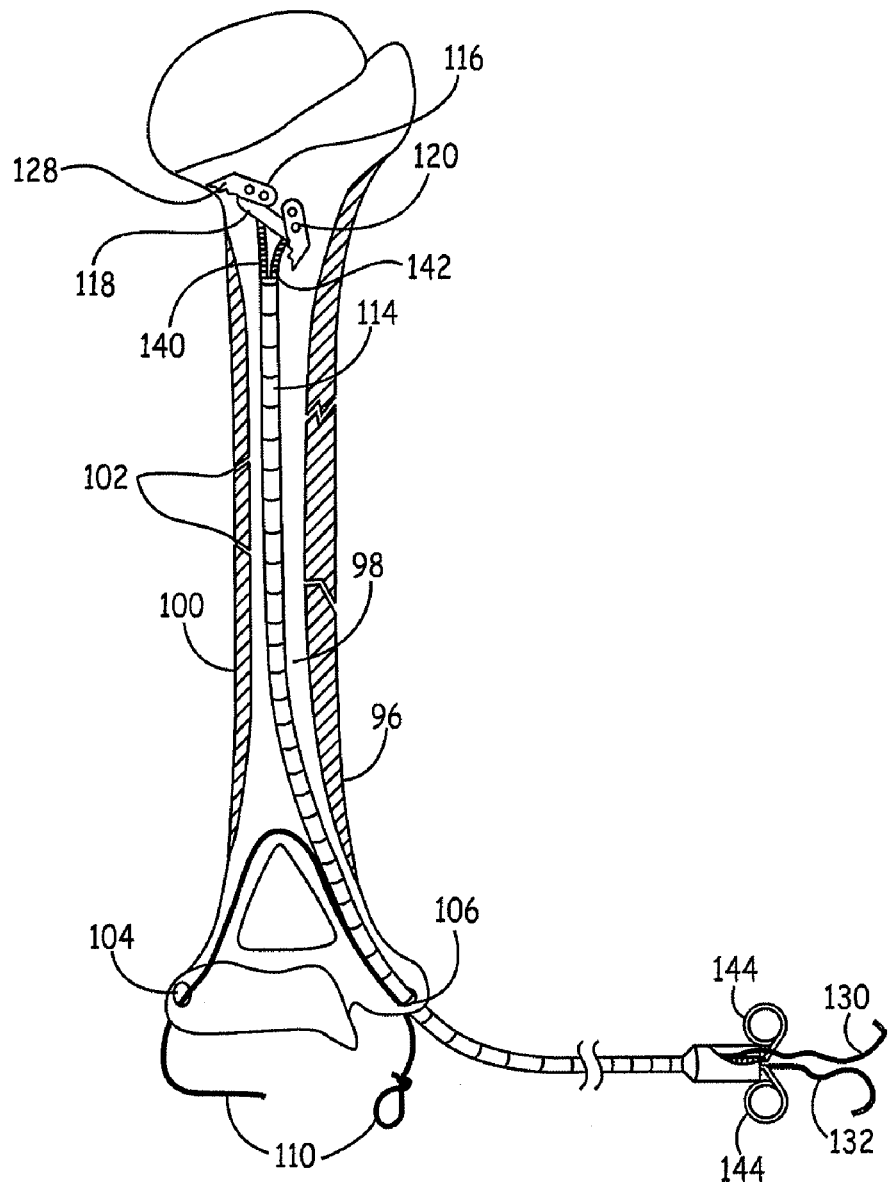
Figure 14E:
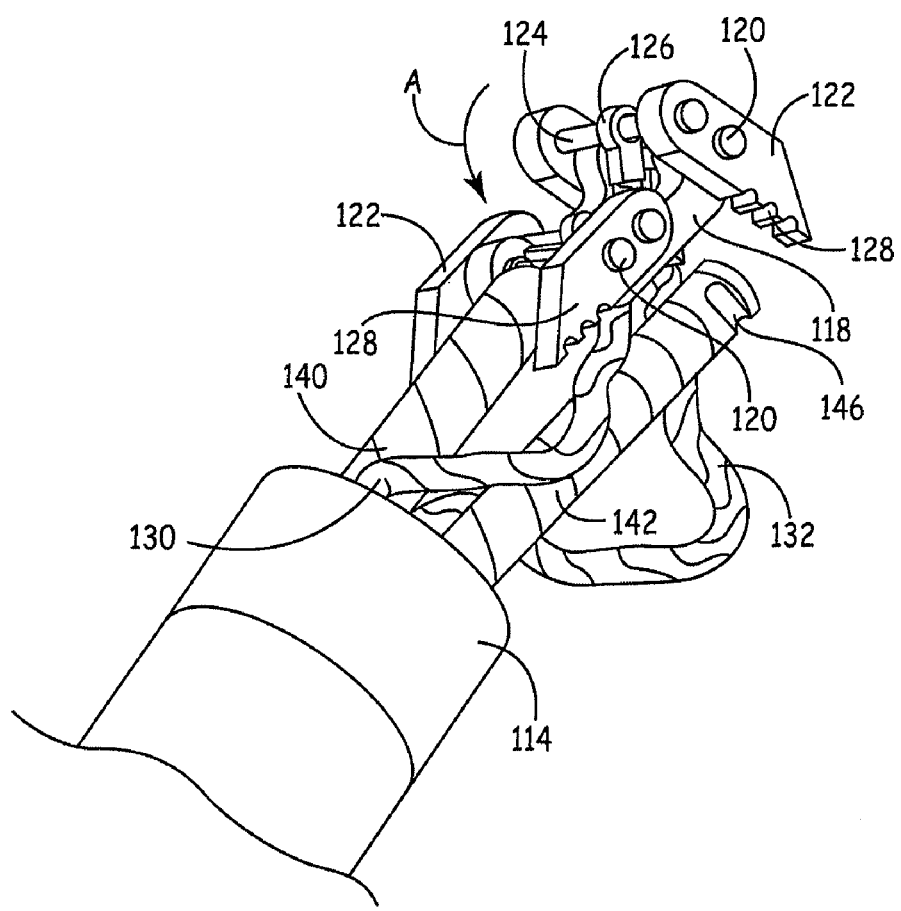

Referring to FIG. 14E, the toggle mechanism typified in the drawing has a body formed of a pair of parallel, spaced, elongated body strips 118 joined at their ends by transverse pins 120. Two pairs of parallel gripping arms 122 are provided, the arms of each pair being spaced and joined at their ends by a rod 124, and it is to these rods extending between the arms 122 of each pair that the ends of the cords 130 and 132 are respectively attached through the use of eyelet connectors 126. The pins 120 that join the body strips 118 also pass outwardly through holes formed in the gripping arms intermediate their ends so that the gripping arms can pivot about the pins between extended and articulated orientations. Each gripping arm has an end 128 opposite the ends joined by the rods 124 that is serrated or otherwise configured for gripping to bone.

To properly position the toggle 116, a pair of flexible push rods 140 and 142 are provided within the introducer tube 114, each push rod extending outwardly of the introducer tube as shown in FIG. 14D and being attached to manually graspable rings 144 that permit the push rods 140 and 142 to move axially and also rotationally. The push rods 140 and 142 may have transverse grooves, as shown at 146 in FIG. 14E, adjacent their ends, the grooves 146 being sized to receive the transverse pins 120. The grooves 146 may be disengaged from the pins 120 simply by rotating the push rods through 90 degrees. One thus may position the toggle 116 as desired within the medullary canal through relative axial movement of the push rods 140 and 142, and once the body of the toggle 116 is in its desired location, the push rods may be rotated to disengage them from the toggle 116 so that they can be removed. Moreover, once the body of the toggle 116 has been oriented as desired, and optionally before removal of the push rods, 140 and 142 tension is placed on the cords 130 and 132, causing the arms 122 to pivot in the direction of the arrow A in FIG. 14E to cause the ends 128 of the arms 122 to extend outwardly of the toggle body as shown best in FIG. 14F into gripping contact with bone on each side of the medullary canal.

Returning now to FIG. 14C, the flexible introducer tube 114, including within it the toggle 116 to which are connected the pair of flexible cords 130 and 132, is pushed upwardly through the medullary canal to a point at which anchoring of the cords 130 and 132 is desired, this, in FIG. 14D, generally being near the head of the humerus where the medullary canal becomes wider. The toggle 116 is held in place within the medullary canal by the push rods 140 and 142 attached to the transverse pins 120 of the toggle body, and the flexible tube 114 is withdrawn slightly to expose the toggle 116 within the medullary canal. By appropriate axial movement of the push rods, 140 and 142 the toggle arms ends 128 are deployed outwardly into contact with the bone. Once approximate deployment of the toggle 116 has been accomplished, the flexible tube 114 may be removed distally through the hole 106. Further manipulation of the push rods 140 and 142 with respect to each other and to the bone may be required to achieve proper orientation of the toggle 116 within the medullary canal. A 90 degree twist of each push rod 140 and 142 frees it from the toggle and enables the push rods 140 and 142 to be individually removed from the medullary canal. Of course, in this and other procedures described herein, fluoroscopy may be used to insure proper placement of elements of the cord system.

At this point, it will be noted that both of the flexible, inelastic cords 130 and 132 exit from the hole 106. The wire 110 with a formed loop at one end is attached to one of the cords, cord 130 in this example. Pulling the wire 110 from the hole 104 draws the fastened cord 130 outwardly through the hole 104.

Figure 14F:
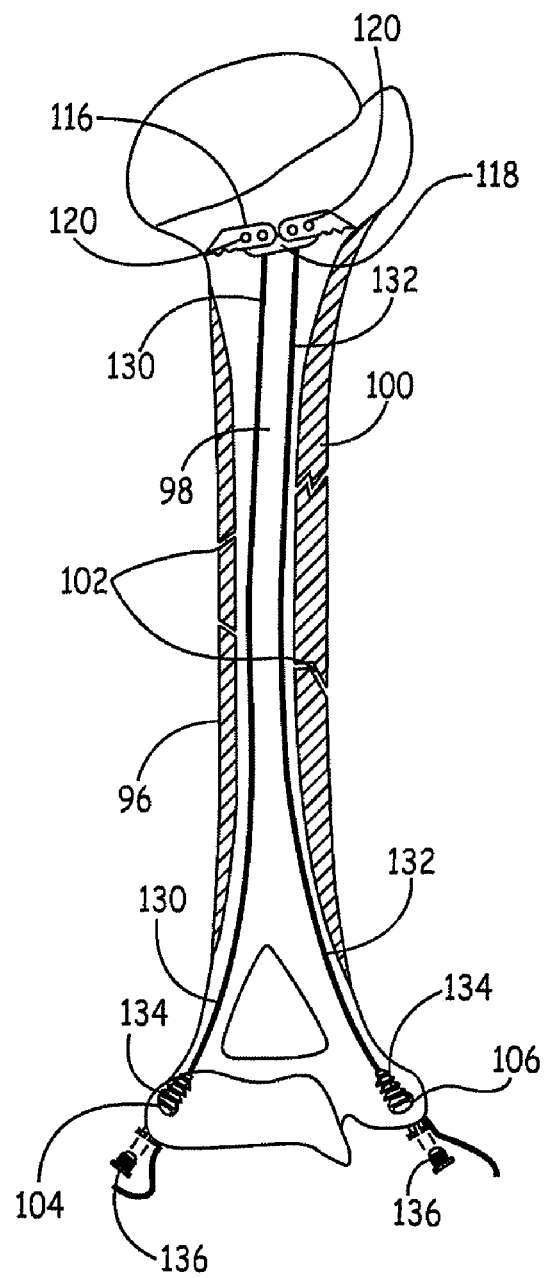

FIG. 14F shows the flexible, inelastic cord system in place in the humerus, the toggle 116 being firmly anchored near the head of the humerus, the flexible, inelastic cords 130 and 132 extending in a spaced orientation downwardly through the medullary canal with cord 130 exiting from the medullary canal through the hole 104 and cord 132 exiting from the other hole 106. External fasteners of the type described above in connection with FIG. 2 and designated 134 are screwed into the holes 104 and 106 with the cords 130 and 132 extending therethrough. By suitably pulling on the cords 130 and 132 from the distal end of the humerus, the fracture surfaces may be brought together as desired. By spacing the cords 130 and 132 from one another, the possibility of placing one side of the bone in tension and the other in compression is largely avoided. Once the fracture surfaces have been appropriately located, the locking screws 136 are screwed into the ends of the fasteners 134, locking the cords 130 and 132 in place. Because the cords 130 and 132 are inelastic, any tension remaining in the cords 130 and 132 after attachment of the locking screws 136 is quickly lost.

While the cord system is effective in treating bone fractures, it may require augmentation as the end of the long bone is approached, where it is necessary to deal with the tension forces of the ligaments and tendons. Tubular supports may be used in conjunction with the inelastic cords of the cord fracture fixation device to provide at least temporary compressive resistance to the cord until new bone is formed.

Cancellous bone is elastically compressible and a rod, or a screw and plate, inhibits its normal function. Further, cortical bone with a screw across its cavity acts as a rasp when the long bone is flexed. That is, when a long bone is flexed in the plane of a screw, the diameter of the bone decreases as the circular cross section of the bone becomes oval. This shortening of the diameter, or micro-motion, may contribute to the loosening of screw fixation, especially in more flexible bone and with greater flexing forces on the bone, with early weight bearing. The cord of the cord system has substantially no compression resistance and the cord with a tubular support, the support being elastically compressible, neutralizes and modifies this effect. This lessens the need for a neutralizing plate, commonly used in the screw fixation of fractures.

The tubular supports aid a surgeon in recreating the transition of forces in the largely cancellous ends of long bones and to fix fractures in largely cancellous bones such as the Os Calcis or pelvis. The tubular supports may further be used to at least partially reduce or contain particulate shedding. Particulate shedding is contained by the tube surrounding the cord and reduced by the buffering of the mechanical load and amplitude of cycles.

Figure 15A:
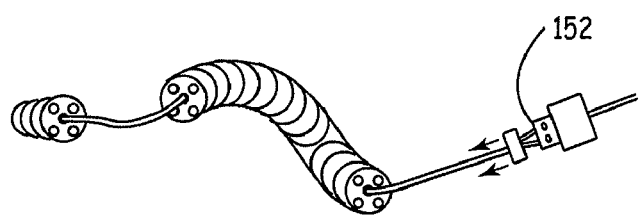
FIG. 15A is a perspective view of the tool for placing a tubular support of the invention.
Figure 15B:
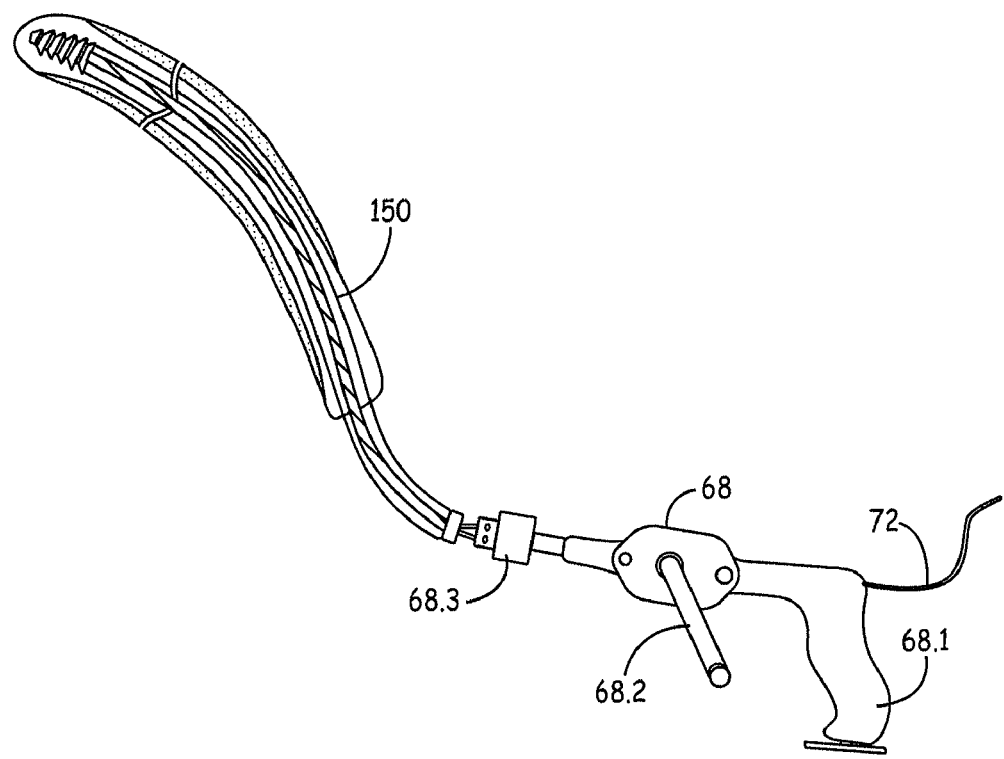
FIG. 15B is a cross sectional view of the pelvis of FIG. 12A showing a step in the reduction of the fracture.
Figure 15C:
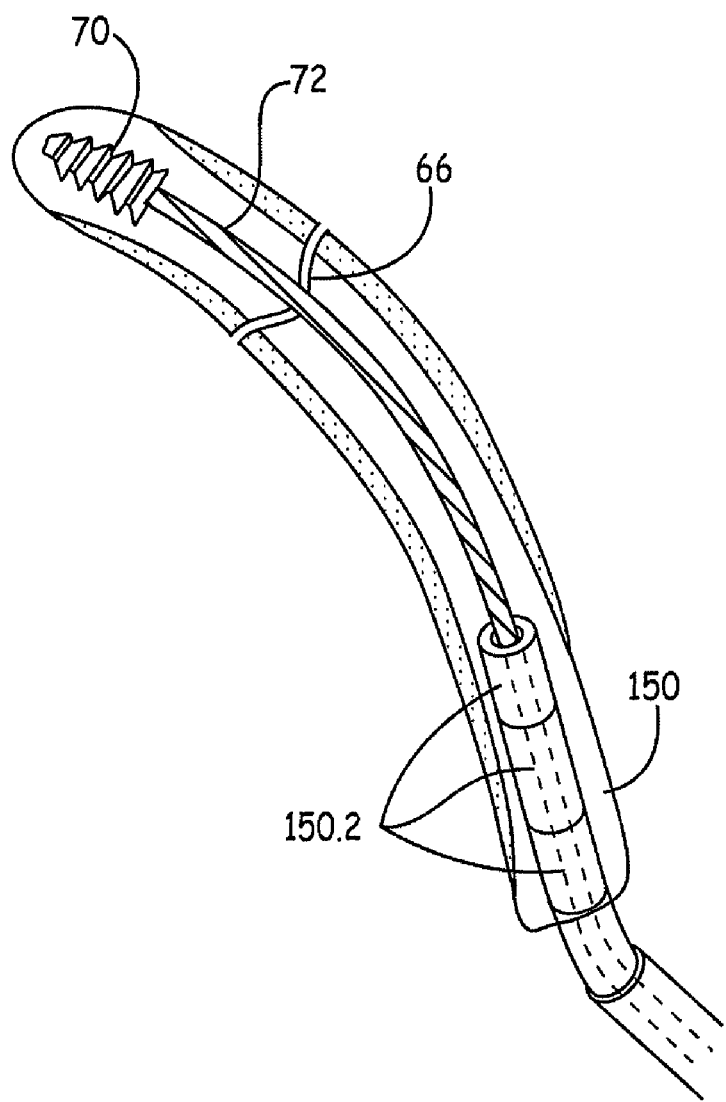
FIG. 15C is a cross sectional view of the pelvis of FIG. 12A showing the reduced bone.

FIGS. 15B-15C show steps in the reduction of a fracture of the ilium of the pelvis using a tubular support 150. The fracture is designated generally as 66 and is shown in FIG. 12A.

FIG. 15A illustrates a tool for placing a tubular support 150. In FIG. 15A, the tool 152 is a four pin drive, the drive including a male end for mating with a female end of the tubular support 150. A proximal end of the tubular support 150 is shaped to receive the male end of the drive, such as a slot or four pins, to allow the drive to rotate the support, thereby aiding its insertion into the bone, over a cord of the present invention. Of course, any other tool suitable for placing the tubular support may be used.

A tubular support of the present invention, for use with the cord fracture fixation device is preferably made of a material softer than bone and capable of accepting compressive stress without plastic deformation strain. Preferably, the elastic compression of the tube should be approximately equal to that of cancellous bone in the cavity of the end of the bone. Suitable materials for the tubular support include, for example, methyl methacrylate or poly lactic acid.

The tubular support may be made up of a series of segments or may be a single segment. Further, the tubular support may be smooth, threaded, or alternately smooth and threaded. Generally, the use of a threaded tubular support aids in grip and the transmission of forces to the cancellous bone. Additionally, providing a series of segments of tubular supports better allows the tubular supports to be introduced along the cord as it curves, for example, between the outer cortical bone and around the acetabulum. After any curved portion of the cord has been covered, smooth tubular supports and larger segments may be used. Preferably, the first threaded tubular support is attached to the bone ends in the region where the ligaments and tendons attach. For example, in the case of a pelvic facture, it is preferable that the first threaded tubular support attach primarily in the Sacroiliac joint region and the Symphysis pubis regions.

The tubular support 150 has a diameter larger than that of the cord such that it surrounds the cord loosely, allowing movement of the tubular support over the cord. The diameter of the tubular supports and the smaller diameter of the cord allows material to be introduced along the length of the cord as it remains in-situ. The introduced liquid material tends to exit in the areas where the tubular support is segmented, especially with nonconforming adjacent surfaces. A fenestrated segment may be provided to further aid material delivery to one area, as well as reducing the resistance to axial compression in that area which may have a pumping effect. Antibiotics may be incorporated into the structure of methyl methacrylate bone cement to allow gradual diffusion over a period of time rather than liquid injection down the central canal of the cord. Further, removal of the cord at a later stage may allow the liquid delivery to be achieved at that time.

In the embodiment of FIG. 15B, the tubular support 150 is threaded. Preferably, the threading matches the thread diameter of the internal fastener 70, for example, that of FIG. 12B such that the tubular support 150 may follow the path of the threaded fastener 70 through the cortical bone. By providing matching thread diameters, the tubular support 150 may follow the path created by the threaded fastener 70 through the cancellous bone. When necessary, for example, when the outer bone is particularly thick, a drill hole the size of the shank and a tap with the same thread configuration as the threaded tubular support may be used to develop the thread pattern. Non-threaded tubular supports are preferably the diameter of the shank so that they can be pushed into the path without disturbing the thread pattern, particularly at the outer cortex where the final element is fixed and a larger thread pattern may be required to compensate for damage.

FIG. 15C illustrates a tubular support 150 comprising a series of segments 150.2 inserted over the cord 72 of FIG. 12C. The series of segments 150.2 may be of the same or different lengths, and provide a variable flex pattern to the tubular support 150. Typically, as shown in FIG. 15C, the ends of each segment 150.2 is cut at 90 degrees. However, the ends of each segment may be cut at different angles to provide a preferred resting position of the segments 150.2 when the cord 72 is tensioned. Of course, a tubular support 150 comprising a single segment 150.2 may be provided in lieu of the series of segments 150.2 of FIG. 15C.

The final tubular support segment is preferably threaded to engage the outer bone, the outer bone being primarily cortical bone. It is desirable that at least the final segment be manufactured of a material having sufficient strength to lock the cord in place. The threaded element engages the cortical bone and the threaded tubular support engages the cancellous bone. Thus, the cortical bone of a first fragment, the first threaded element, the cancellous bone of the first fragment and tubular support are fixed as a block. A similar block is fixed at the second bone fragment, the threaded tubular support extending from the near cortex. At this stage, screwing the threaded tube further into the bone causes it to protrude from the near cancellous bone and, traveling along the cord, push the block of the first fragment away, to open the fracture, or correct the collapse of the first block inwardly where there is bone loss or instability. When this adjustment is complete, the cord is tensioned to neutral and fixed with a set screw to the second bone fragment. Thus, the length of the final segment is determined by the characteristics desired of the cord fixation system. The final segment may be sufficiently long such that when it abuts the previous segment in the series, it still projects from the cortex or outer bone. Thus, rotation of the final segment when it is not engaged with the previous segment will result in distraction of the last cortex from the first.

In another embodiment, the final segment may be relatively short, leaving a space between the final segment and the previous segment. Thus, when the final segment is flush against the cortical surface, tension on the cord will act to draw the separated segments together, compressing the last cortex towards the first. The exact configuration of the tubular support thus can be used to adjust and maintain the distance between two or more bone fragments, providing a strut that has both length and flexural characteristics. These characteristics are particularly desirable in softer bone and where an area of bone loss is being bridged.

FIGS. 16A and B show reduction of a fracture of the humerus or other long bone using inelastic cords and at least one tubular support 150. The fracture of FIG. 16A mirrors the fracture of FIG. 14A, the humerus designated 96 and including a medullary canal 98 bounded by cortical bone 100. Long bones typically have cartilage, e.g. joint surface, and ligaments to stress one end of the bone.

Similarly, the cord system of the present invention can be used with the upper tibia where the cord can be introduced directly across the bone. The tibial plateau is supported on both sides of the fracture by a cord with a threaded tubular support. When the cord is tensioned, the threaded tubular support grips the thin cortical bone, with the fibrous ligaments and tendinous tissues, and exerts a force to move the threaded tubular support and its surrounding cancellous bone to that of the other side.

In FIG. 16A, cords are separately deployed through each of the holes 104 and 106. Flexible, hollow introducer tubes 114 carrying toggles 116, as in FIGS. 14C and 14F, also seen in FIG. 16B are deployed through the holes 104 and 106. After the toggles are fixed (as described in reference to FIGS. 14A-14F), the flexible tubes 114 may be removed distally through their respective holes 104 and 106.

As seen in FIG. 16B, with the flexible, inelastic cord system in place in the humerus, the toggle 116 is firmly anchored near the head of the humerus and the flexible, inelastic cords 130 and 132 extend in a spaced orientation downwardly through the medullary canal with cord 130 exiting from the hole 104 and cord 132 exiting from the other hole 106. A tubular support 150, here comprising a series of segments 150.2, may be inserted over the cords 130 and 132 through the holes 104 and 106. The tubular support 150 covers the cords 130 and 132, thereby reducing any particulate shedding. Further, the tubular support 150 provides an at least temporary compressive resistance to the cords 130 and 132 until new bone is formed. If desired, an antibiotic or pharmaceutical may be provided within the material of the tubular support 150 for slow diffusion. Tubular supports 150 may be introduced over the cords 130 and 132 through pressure driving.

As with respect to FIGS. 14A-14F, external fasteners of the type described in connection with FIG. 2 and designated 134 are screwed into the holes 104 and 106 with the cords 130 and 132 extending therethrough. By suitably pulling on the cords 130 and 132 from the distal end of the humerus, the fracture surfaces may be brought together as desired. Locking screws 136 are screwed into the ends of the fasteners 134, locking the cords 130 and 132 in place and preventing the tubular support 150 from extruding. The composite formed by the inelastic cords 130 and 132 and of elastic tubular support 150 creates a fixation construct that is variable and may treat fractures in cancellous and cortical bones.

Figure 17A:
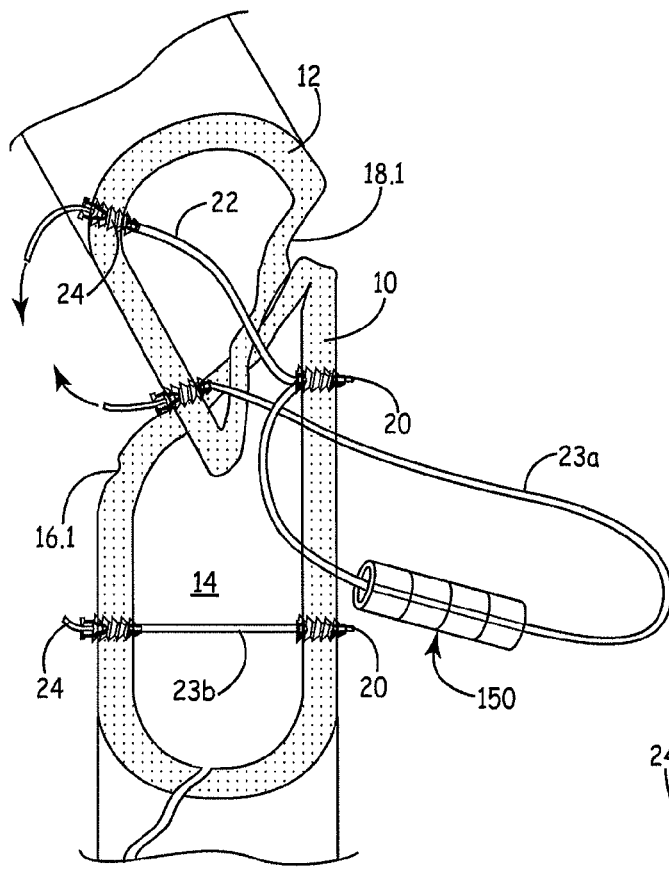
FIG. 17A is a partial cross sectional view of a fractured bone to which a cord fracture fixation device of the invention is being applied to reduce the fracture.
Figure 17B:
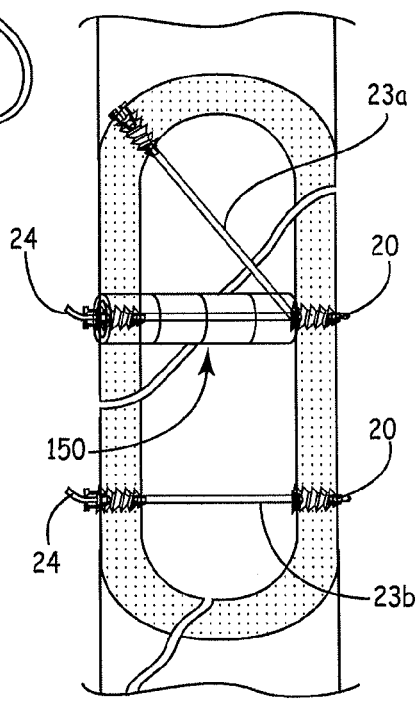
FIG. 17B is a partial cross sectional view of the bone of FIG. 17A showing the reduced bone.

FIGS. 17A and 17B show reduction of a fractured bone similar to that shown in FIG. 1. Internal fasteners 20 and external fasteners 24 are positioned such that when a cord 23A or 23B is placed in tension, the fracture surfaces 16.1 and 18.1 will be brought together at a fracture interface with the interface being maintained under compression so long as the cord 23 is maintained in tension. A tubular support 150, comprising a single or a series of segments, is positioned over all of or a portion of the cord. FIG. 17B illustrates a tubular support 150 positioned over a portion of cord 23A. The tubular support 150 functions to provide compressive resistance.

The invention is particularly adapted for use in situations in which a bone has been fractured into a number of fragments that need to be carefully brought back into alignment, with compression being generated at the fracture interfaces during physical activity to promote fracture healing. The use of external splints, casts, bandages, cerclage elements, and the like to reduce fractures in badly fractured bones is quite difficult. Exterior pressure must be used to force bones into the correct position and continued adequate compression of all or most of the fracture interfaces is difficult to attain. Through the use of the invention, in which fasteners are placed into bone fragments from the interior of the bone, with flexible cords being employed within the bone, to pull, rather than push, the fragments into place, the force vectors needed for proper fracture reduction and interface compression can be readily chosen at the time of surgery. Additionally, tubular supports may be provided over the inelastic cords, providing a variable fixation construct, and providing compressive resistance to the cable. When many bone fragments are involved, a surgeon may find it desirable to lead two, three or more cords out of the opening formed in one fragment with the interior ends of the cords attached to the variety of fragments via internal fasteners, the surgeon then operating the cords independently of each other to move the bone fragments into the desired position using fluoroscopy as needed to visualize the cords and proper placement of the bone fragments. The use of a cord having a degree of radiopacity aids visualization of the cord. The cord may be stainless steel to provide radiopacity. A tubular support, comprising a single segment or a series of segments, may be introduced over each or any of the cords. Radiopaque dies such as intravenous dyes used for angiography may be injected down the center of the tubular supports along the cord to demonstrate the cord cavity and openings caused by the segmenting of the tubular supports and/or the fenestrations in the section of tubular support used to deliver liquid therapeutic agents. This injection process may be anticipated at the time of fracture fixation, and a tube inserted into the final tubular support provided with a channel that connects to the central conduct that houses the cord. This tube may be brought through the would to the skin surface to aid the delivery process typically over the two weeks following fracture fixation.

While a preferred embodiment of the present invention has been described, it should be understood that various changes, adaptations and modifications may be made therein without departing from the spirit of the invention and the scope of the appended claims.

The invention claimed:

1. An orthopedic fixation system for fixing a bone having an exterior cortical portion and a non-cortical interior portion to an element which is a bone fragment or a prosthesis, comprising a length of flexible, inelastic cord; a first fastener for attaching the cord to said element; a second fastener for attaching the cord to the bone and enabling the cord to extend from said first fastener within the non-cortical interior of the bone to the second fastener, at least one of the fasteners having an opening through which the cord may pass from the interior of the bone to the exterior to enable said element to be securely mounted to the bone portion, and an axially rigid tubular support that includes pharmaceuticals for release into the fracture site and is sized to permit the cord to extend through it the at least one fastener including a lock for locking the cord to the fastener through which it passes, wherein the opening comprises a bore at least partially threaded and within which the cord extends, and wherein the lock comprises a threaded member threadingly received in the bore and capable of engaging the cord to restrain cord movement.

2. The orthopedic fixation system of claim 1, wherein the tubular support comprises a series of segments.

3. The orthopedic fixation system of claim 2, wherein at least one of the segments is threaded.

4. The orthopedic fixation system of claim 1, wherein the tubular support is threaded.

5. The orthopedic fixation system of claim 1, wherein the tubular support is sized such that the bone and the bone fragment or prosthesis are distracted from one another.

6. The orthopedic fixation system of claim 1, wherein the tubular support is sized such that when the tubular support is flush against a cortical surface of the bone, tension on the cord will draw the bone and bone fragment or prosthesis together.

7. The orthopedic fixation system of claim 1, wherein the pharmaceuticals includes antibiotics.

8. The orthopedic fixation system of claim 1, wherein at least one of the fasteners includes a threaded port ion adapted to be screwed into bone.

9. The orthopedic fixation system of claim 1, wherein the element is a bone fragment resulting from a fracture of the bone, the bone fragment and bone having mating fracture surfaces that are prevented from separating by the cord extending between them.

10. The orthopedic fixation system of claim 9, wherein at least one of the fasteners includes an elongated toggle portion adapted to pass in a generally coaxial direction through a bore formed in the bone or bone fragment and to assume a position generally normal to the axis against an outer surface of the bone or bone fragment.

11. The orthopedic fixation system of claim 9, wherein at least one of the fasteners includes a threaded portion adapted to be screwed into bone.

12. The orthopedic fixation system of claim 9, wherein at least one of the fasteners includes a bone plate adapted to engage a bone surface.

13. The orthopedic fixation system of claim 9, further including a third fastener fastenable to bone and having a surface within said interior over which said cord may be movably trained to change the direction of said cord between the first and second fasteners.

14. The orthopedic fixation system of claim 9, wherein at least one of the fasteners includes an opening through which the cord passes from the interior of the bone to the exterior, the at least one fastener including a lock for locking the cord to the fastener through which it passes.

15. An orthopedic fixation system for fixing a bone having an exterior cortical portion and a non-cortical interior portion to an element, the element being a bone fragment resulting from a fracture of the bone, the bone fragment and bone having mating fracture surfaces that are prevented from separating by a cord extending between them, comprising a length of flexible, inelastic cord; a first fastener for attaching the cord to said element; a second fastener for attaching the cord to the bone and enabling the cord to extend from said first fastener within the non-cortical interior of the bone to the second fastener, at least one of the fasteners having an opening through which the cord may pass from the interior of the bone to the exterior to enable said element to be securely mounted to the bone portion, and an axially rigid tubular support sized to permit the cord to extend through it, at least one of the fasteners includes an opening through which the cord passes from the interior of the bone to the exterior, the at least one fastener including a lock for locking the cord to the fastener through which it passes, wherein the opening comprises a bore at least partially threaded and within which the cord extends, and wherein the lock comprises a threaded member threadingly received in the bore and capable of engaging the cord to restrain cord movement.

16. The orthopedic fixation system of claim 1, further including a tensioning instrument adapted to contact the cord and at least one of said fasteners to place the cord in tension by drawing the cord outwardly through said fastener.

17. A bone fracture reduction system for promoting healing of a bone fracture of a bone normally having an exterior cortical portion and a non-cortical interior portion and having bone fragments with generally confronting fracture surfaces, comprising an internal fastener attachable from within the non-cortical interior to a first bone fragment, a second fastener attachable to a second bone fragment, a length of flexible, inelastic cord having substantially no axial compressive strength and extendable within said bone interior and attached to said internal fastener and the second fastener, the internal fastener, the second fastener, and the cord being so positioned as to draw respective fracture surfaces together to reduce the fracture upon tensioning of the cord between the internal fastener and the second fastener, and an axially rigid tubular support sized to permit the cord to extend through it, wherein the second fastener is an external fastener having a hollow interior through which the cord extends, the hollow interior being at least partially threaded, and further including a lock comprising a threaded member threadingly received in the hollow interior, the cord being operatively grasped between the threaded member and the hollow interior to restrain cord movement within the second fastener.

18. The bone fracture reduction system of claim 17, wherein the tubular support includes pharmaceuticals for release into the fracture site.

19. The bone fracture reduction system of claim 17, wherein the tubular support includes antibiotics for release into the fracture site.

20. The bone fracture reduction system of claim 17, wherein the tubular support comprises a series of segments.

21. The bone fracture reduction system of claim 17, wherein the tubular support is sized such that when the tubular support is flush against one of the bone fragments, tension on the cord will draw the first and second bone fragments together.

22. The bone fracture reduction system of claim 17, further including a lock to restrain cord movement within the second fastener.

23. The bone fracture reduction system of claim 22, wherein the internal fastener includes a threaded portion screwed into the cortical portion from within the bone interior.

24. The bone fracture reduction system of claim 17, wherein the first bone fragment has an outer, cortical surface and wherein the first fastener includes an elongated toggle supported against the outer surface portion.

25. The bone fracture reduction system of claim 17, wherein the bone is a long bone having a medullary cavity, the internal fastener being attachable from within the medullary canal to one of the bone fragments and the length of flexible, inelastic cord extending from the internal fastener through the external fastener across a fracture interface and more closely adjacent one side of said medullary canal than the other side thereof, the bone fracture reduction system including a second flexible, inelastic cord and a third fastener, the third fastener being an external fastener and being attachable to the second bone fragment and through which the second cord extends, the second cord being arranged on generally the opposite side of said medullary canal from the first cord, whereupon the cords may be independently adjusted so as to resist bending moments applied at the transverse fracture site.

26. The bone fracture reduction system of claim 25, wherein the internal fastener comprises a pair of fasteners each having threaded portions threaded into the first bone fragment on opposite sides of the medullary canal.

27. The bone fracture reduction system of claim 25, wherein the internal fastener comprises an elongated fastener adapted for insertion and capture within the medullary canal of the first bone fragment with the cords extending from the fastener adjacent opposite sides of the intermedullary canal.

28. The bone fracture reduction system of claim 17, wherein one bone fragment has a bore extending through its cortical portion and wherein the second fastener includes a plate adapted to engage the outer surface of the cortical portion of that bone fragment.

29. The bone fracture reduction system of claim 17, further including a third fastener attachable from the interior of the bone to a third bone fragment and having a pulley surface over which the cord may be movably trained to change the direction of the cord within the interior of the bone.

30. The bone fracture reduction system of claim 29, wherein at least one of the internal fasteners includes a pulley surface over which the cord is movably trained to change the direction of the cord within the interior of the bone.

31. The bone fracture reduction system of claim 17, further including a plurality of internal fasteners attachable from within the bone interior to different ones of the bone fragments, wherein the fasteners and cord may be positioned so as to draw respective fracture surfaces of the bone fragments together to reduce the fracture upon tensioning of the cord.

32. A method for positioning fragments of a bone fracture with respect to each other to reduce the fracture and promote healing of a bone which normally has an exterior cortical portion and a non-cortical interior portion, the bone fragments having confronting fracture surfaces forming a fracture interface, the method comprising screwing an internal fastener that that has a threaded end from within the interior of the bone into a cortical portion of a first bone fragment an internal fastener to which is attached a length of flexible, inelastic cord, advancing an axially rigid tubular support over the cord, and drawing the cord through a bore formed in a second bone fragment to draw the fragments together in a direction to relieve the fracture, wherein the tubular support contacts and extends between the first and second bone fragments.

33. The method of claim 32, wherein the step of advancing an axially rigid tubular support over the cord comprises advancing a series of segments together forming the tubular support over the cord.

34. The method of claim 32, further including the step of positioning the tubular support flush against one of the bone fragments, the tubular support being sized such that such positioning causes tension on the cord to draw the first and second bone segments together.

35. The method of claim 32, further including the step of positioning the tubular support such that the first and second bone fragments are distracted from one another.

36. The method of claim 32, wherein the tubular support includes pharmaceuticals for release into the fracture site.

37. The method of claim 32, wherein the tubular support includes antibiotics for release into the fracture site.

38. The method of claim 32, further including the step of securing the cord to the second bone fragment to restrain separation of the bone fragments at the fracture interface.

39. The method of claim 32, further including the step of determining the direction of tensile force desired to draw the fracture surfaces toward each other, and positioning the cord parallel to that direction.

40. The method of claim 32, wherein the internal fastener has an elongated toggle portion, the method including the step of forming a bore through the first bone fragment, and passing the toggle from the interior of the bone through the bore in the first bone fragment to position the toggle to lie against a cortical outer surface of the first bone fragment.

41. The method of claim 32, wherein the step of drawing the cord through a bone formed in a second bone fragment includes attaching to the second bone fragment an external fastener, drawing the cord through the external fastener, and locking the cord to the external fastener.

42. The method of claim 41, further including the step of tensioning the cord by grasping the cord with a first portion of a tensioning instrument, contacting the external fastener with a second portion of the tensioning instrument, and operating the instrument so as to separate the first portion from the second portion.

43. The method of claim 32, further comprising the step of attaching a plurality of internal fasteners to different ones of a plurality of bone fragments, the flexible, inelastic cord being attached to each of the internal fasteners, wherein a plurality of axially rigid tubular supports are advanced over the cord, and positioning the plurality of internal fastener such that when the cord is tensioned, the fragments are drawn together to reduce the fracture.

44. The method of claim 43, wherein at least one of the internal fasteners includes a pulley surface over which the cord is movably trained to change the direction of the cord within the interior of said bone, the method including the step of pulling the cord over the pulley surface.

45. The method of claim 43, wherein each of the internal fasteners includes a pulley surface over which the cord is movably trained to change the direction of the cord within the interior of the bone, the method including the step of pulling the cord over the pulley surfaces.

46. A method for reducing a bone fracture in a bone having a cortical exterior portion and a non-cortical interior portion, the bone having at least three bone fragments in which first and second fragments have first mating fracture surfaces and second and third bone fragments have second, different mating fracture surfaces, the method comprising attaching one end of a length of flexible cord from within the bone interior to the first bone fragment, attaching an internal pulley bearing the cord to the second bone fragment, the other end of the cord passing outwardly of the bone through an opening in the third bone fragment, advancing a first axially rigid tubular support over the cord between the first and second bone fragments and advancing a second axially rigid tubular support over the cord between the second and third bone fragments tensioning the cord to draw together said mating fracture surfaces to relieve the fractures, and securing the tensioned cord to said third bone fragment.

47. A method for reducing a bone fracture comprising at least two pairs of bone fragments, the first pair of bone fragments having first mating fracture surfaces and the second pair of bone fragments having second, different mating fracture surfaces, and wherein one bone fragment may be common to each of the first and second pairs, the bone having an exterior cortical port ion and an interior non-cortical portion, the method comprising a. attaching one end of a length of flexible cord from the interior of the bone to one fragment of the first pair, advancing a first axially rigid tubular support over the cord, and extending the cord through an opening in the other bone fragment of the first pair in a direction so that when the cord is placed in tension, the first mating fracture surfaces are drawn toward each other;

b. attaching one end of a second length of flexible cord from the interior of the bone to one fragment of the second pair, advancing a second axially rigid tubular support over the cord, and extending the second length of cord extending through an opening in the other bone fragment of the second pair in a direction so that when the cord is placed in tension, the second mating fracture surfaces are drawn toward each other; and c. appropriately adjusting tension in the cords with respect to each other to reduce the fracture surfaces.

48. The method of claim 47 including the step of securing the tensioned cords to the other bone fragments.

49. A method for reducing a bone fracture of a bone having a cortical exterior portion and a non-cortical interior portion, the fracture comprising at least three bone fragments each having fracture surfaces mating with fracture surfaces of the other fragments, the method comprising:

a. attaching from the interior of the bone to each of two of the bone fragments a fastener having a pulley surface over which is trained a length of flexible cord;

b. advancing an axially rigid tubular support over the cord;

c. drawing the cord through an opening in a third bone fragment and tensioning the cord to draw the fracture surfaces together; and d. securing the cord to the third bone fragment to reduce the fracture surfaces.

50. Method for reducing a bone fracture of an elongated bone having a medullary canal and a generally transverse fracture dividing the bone into first and second bone fragments, comprising a. attaching from the interior of the bone to one of said bone fragments an internal fastener from which extends at least two flexible, inelastic cord lengths;

b. advancing an axially rigid tubular support over each of the cords;

c. drawing the cord lengths through openings formed in the second bone fragment at spaced positions along the interior of the medullary canal of that fragment so that the cord lengths are spaced from one another within the medullary canal at the fracture site; and d. securing the cords to the second bone fragment to reduce the fracture surfaces, the spaced cords resisting bending moments at the fracture site.

51. A bone fracture reduction system for use in reducing a fracture of a long bone producing first and second bone fragments, comprising an internal fastener adapted to be fastened to the interior of one bone fragment, a pair of flexible, inelastic cords attached to and extending from the internal fastener, a pair of axially rigid tubular supports each sized to receive one of the cords therethrough, and a pair of external fasteners attachable to the other of the bone fragments and having openings through which the cords may respectively pass on opposite sides of the medullary canal, whereby the cords may traverse the fracture site within the medullary canal on opposite sides thereof to resist bending moments at the fracture site.

* * * * *